United States Patent
Igarashi et al.

(10) Patent No.: US 10,314,569 B2
(45) Date of Patent: Jun. 11, 2019

(54) OPERATION FIELD-SECURING DEVICE

(71) Applicant: NIKKISO CO., LTD., Tokyo (JP)

(72) Inventors: Tatsuo Igarashi, Chiba (JP); Yoshihisa Matsunaga, Chiba (JP); Takuro Ishii, Chiba (JP)

(73) Assignee: NIKKISO CO., LTD., Tokyo (JP)

( * ) Notice: Subject to any disclaimer, the term of this patent is extended or adjusted under 35 U.S.C. 154(b) by 0 days.

(21) Appl. No.: 15/559,956

(22) PCT Filed: Jan. 27, 2016

(86) PCT No.: PCT/JP2016/052267
§ 371 (c)(1),
(2) Date: Sep. 20, 2017

(87) PCT Pub. No.: WO2016/152239
PCT Pub. Date: Sep. 29, 2016

(65) Prior Publication Data
US 2018/0103942 A1    Apr. 19, 2018

(30) Foreign Application Priority Data
Mar. 25, 2015    (JP) ................. 2015-062789

(51) Int. Cl.
*A61B 17/02*    (2006.01)
*A61B 17/34*    (2006.01)
*A61M 1/00*    (2006.01)
*A61B 90/40*    (2016.01)
(Continued)

(52) U.S. Cl.
CPC .......... *A61B 17/0218* (2013.01); *A61B 17/02* (2013.01); *A61B 17/0293* (2013.01);
(Continued)

(58) Field of Classification Search
CPC ........ A61B 17/0218; A61B 2017/0225; A61B 2017/0287
See application file for complete search history.

(56) References Cited

U.S. PATENT DOCUMENTS 5,309,896 A * 5/1994 Moll ................ A61B 17/00234
128/898
7,850,600 B1   12/2010 Piskun
(Continued)

FOREIGN PATENT DOCUMENTS

JP    2008-284255 A    11/2008
JP    2013-121478 A    6/2013
(Continued)

OTHER PUBLICATIONS

Apr. 26, 2016 International Search Report issued in International Patent Application No. PCT/JP2016/052267.

*Primary Examiner* — Nicholas W Woodall
(74) *Attorney, Agent, or Firm* — Oliff PLC

(57) ABSTRACT

The present invention provides an operation field-securing device that secures an operation field by being deployed within the body cavity. The operation field-securing device includes at least three elongated parts extending radially in a deployed state; and curved parts, the number of which is the same as that of the elongated parts. Each pair of the two adjacent elongated parts is connected at their one ends by the curved part. Each of the curved parts is convex toward a side opposite to the elongated part. In the deployed state, the curved parts are arranged circumferentially. By deforming the curved parts, the operation field-securing device is capable of being brought into either one of a contracted state where a distance between the adjacent elongated parts is shortened by making the elongated parts close to each other and the deployed state where the distance between the elongated parts is expanded.

18 Claims, 18 Drawing Sheets

(51) Int. Cl.
*A61B 17/00* (2006.01)
*A61B 90/00* (2016.01)

(52) U.S. Cl.
CPC ...... *A61B 17/3423* (2013.01); *A61B 17/3431*
(2013.01); *A61B 90/40* (2016.02); ***A61M
1/0025*** (2014.02); *A61B 17/3474* (2013.01);
*A61B 2017/00862* (2013.01); *A61B
2017/00907* (2013.01); *A61B 2017/0225*
(2013.01); *A61B 2090/378* (2016.02); *A61B
2217/005* (2013.01); *A61B 2217/007*
(2013.01); *A61M 2210/101* (2013.01)

(56) References Cited

U.S. PATENT DOCUMENTS

| | | | | |
|---|---|---|---|---|
| 8,888,695 | B2* | 11/2014 | Piskun | A61B 1/32 600/214 |
| 9,314,267 | B2* | 4/2016 | Piskun | A61B 17/3423 |
| 10,004,388 | B2* | 6/2018 | Saadat | A61M 25/1002 |
| 2006/0074278 | A1* | 4/2006 | Petit | A61B 17/0293 600/224 |
| 2007/0197952 | A1 | 8/2007 | Stiger | |
| 2008/0058650 | A1* | 3/2008 | Saadat | A61B 1/0676 600/478 |
| 2014/0148901 | A1* | 5/2014 | Anderson | A61B 17/0206 623/8 |
| 2015/0080931 | A1 | 3/2015 | Piskun et al. | |
| 2015/0238682 | A1* | 8/2015 | Teranuma | A61B 17/0218 600/205 |
| 2016/0008081 | A1* | 1/2016 | Forsell | A61B 17/3423 600/204 |

FOREIGN PATENT DOCUMENTS

| | | |
|---|---|---|
| JP | 2014-61132 A | 4/2014 |
| JP | 2014-61133 A | 4/2014 |
| WO | 2011/011538 A2 | 1/2011 |

\* cited by examiner

[Fig. 1]
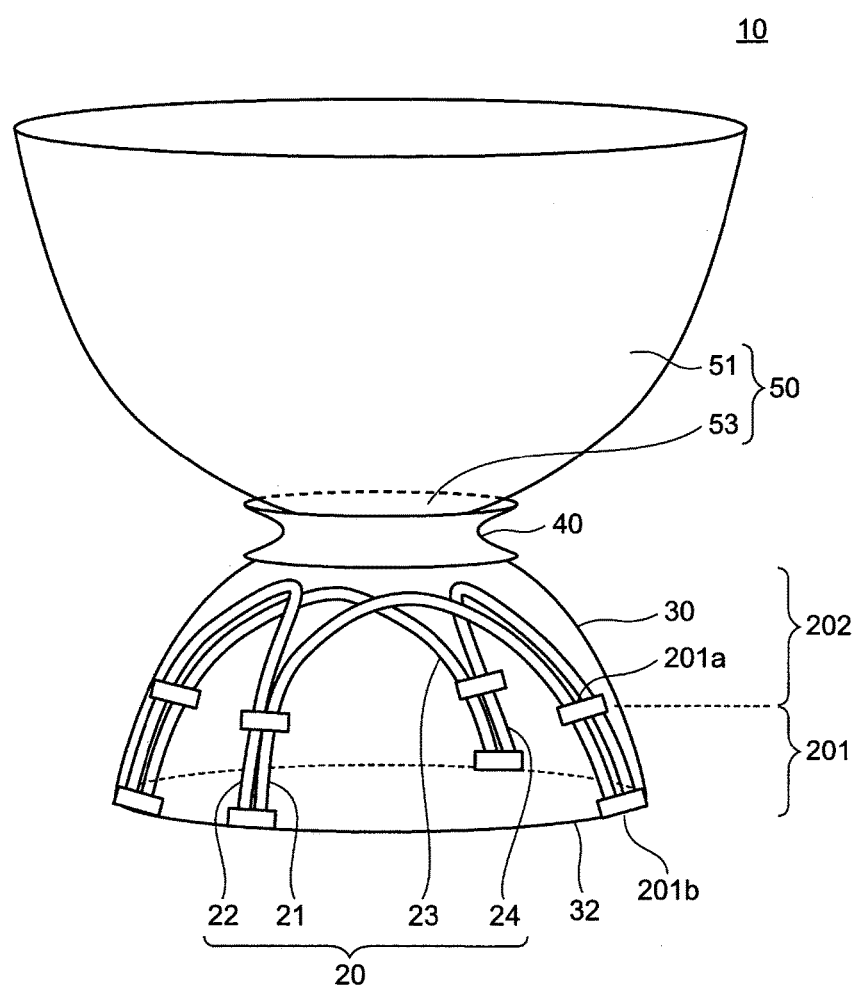

[Fig. 2]
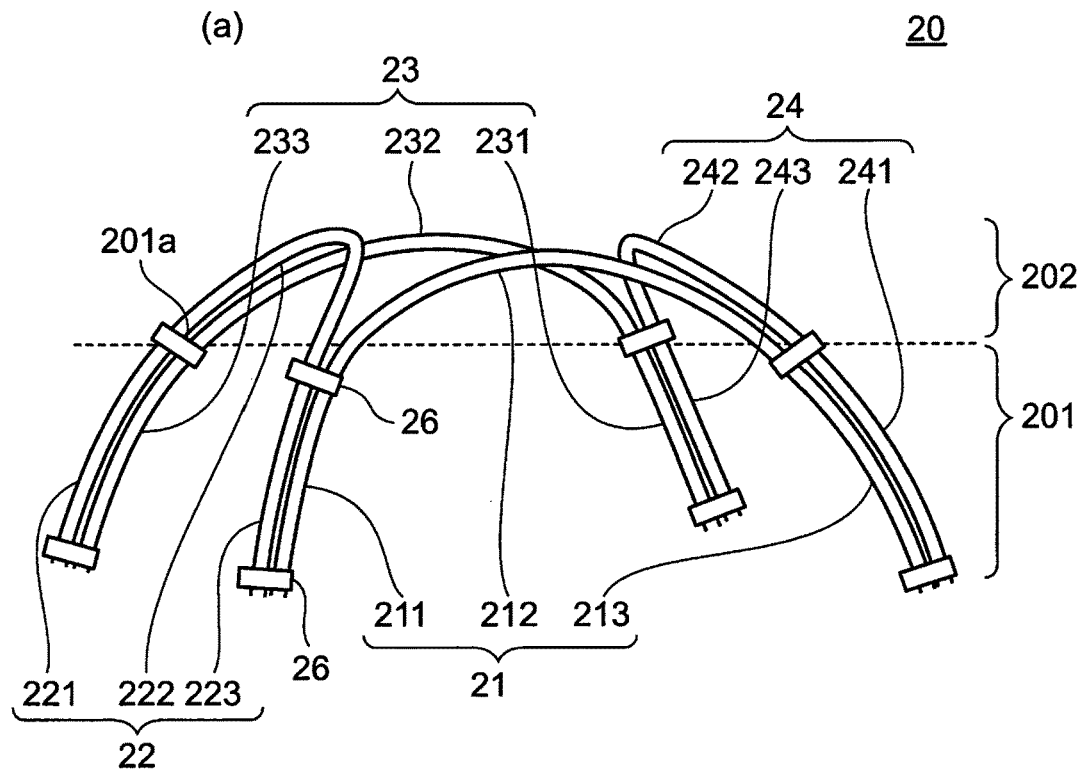
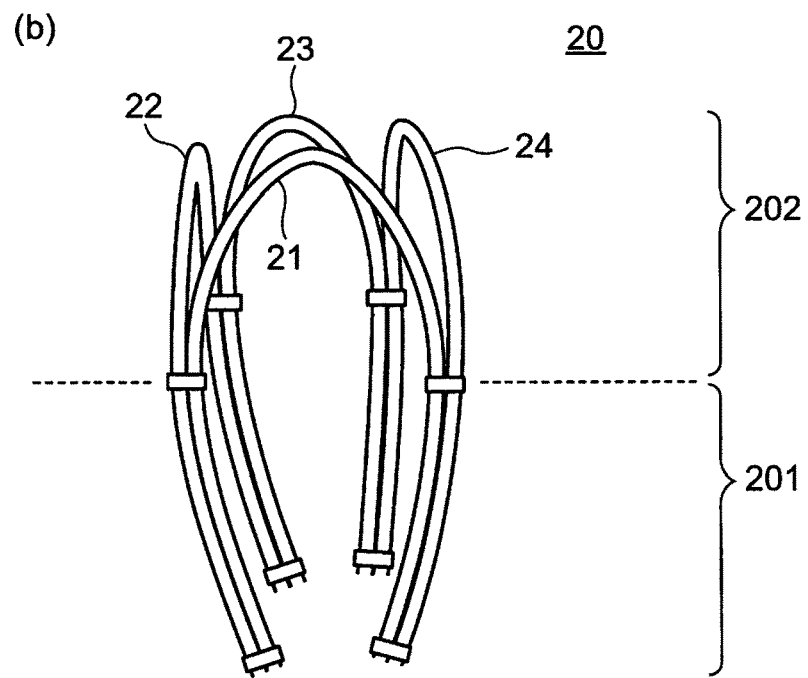

[Fig. 3]
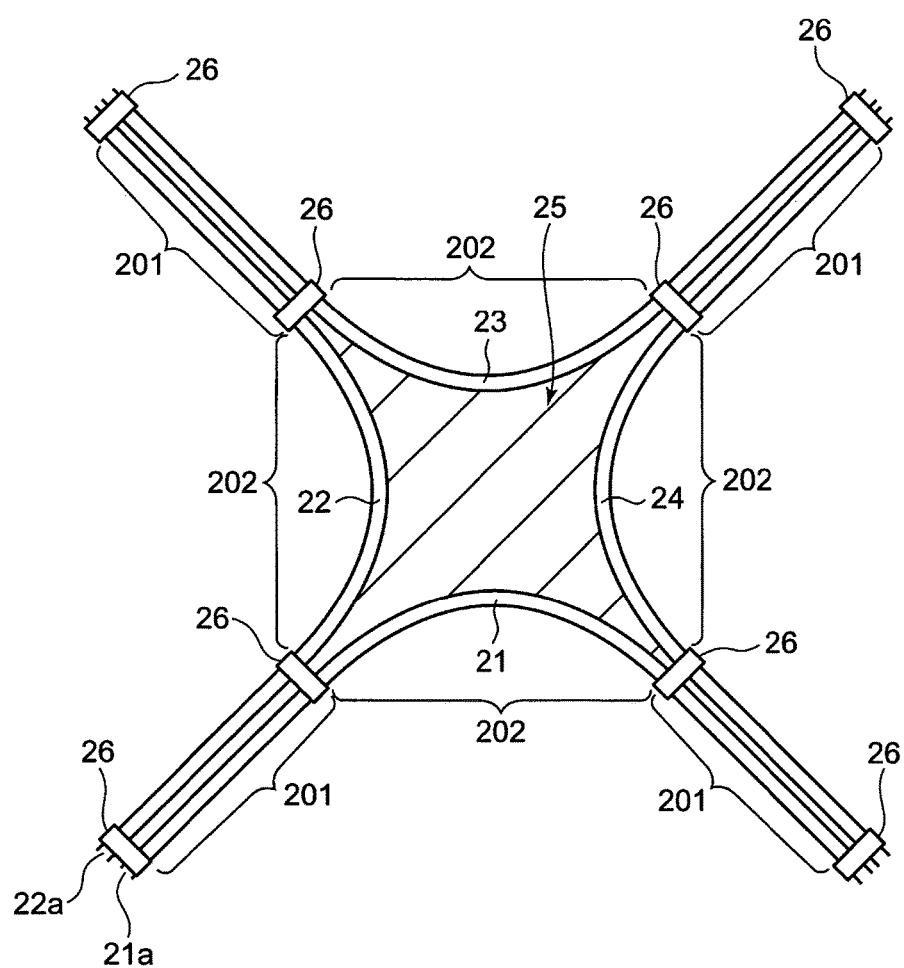

[Fig. 4]
(a)
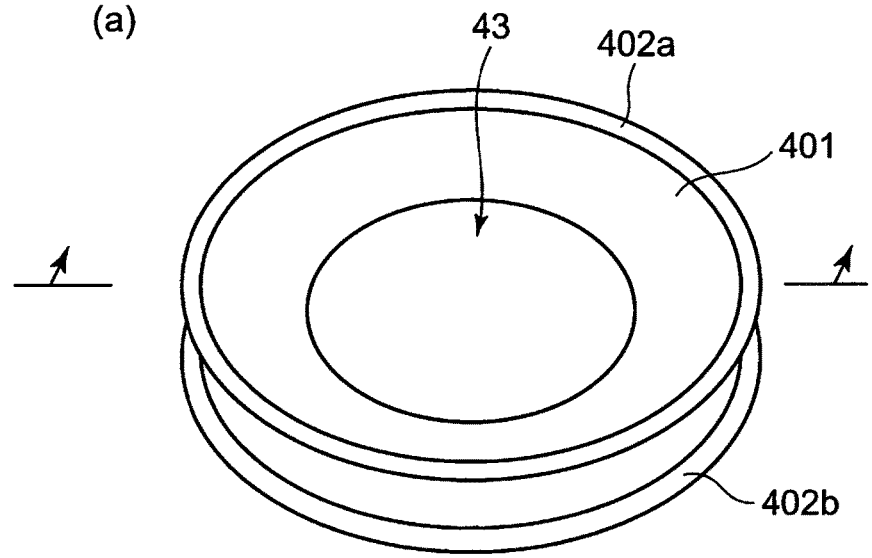
(b)
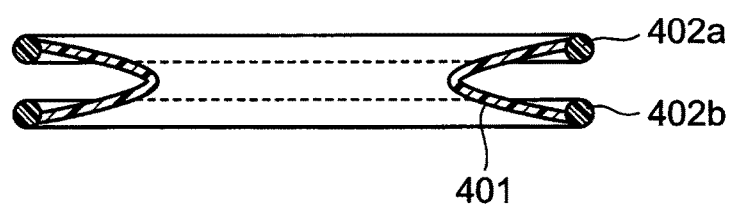

[Fig. 5]
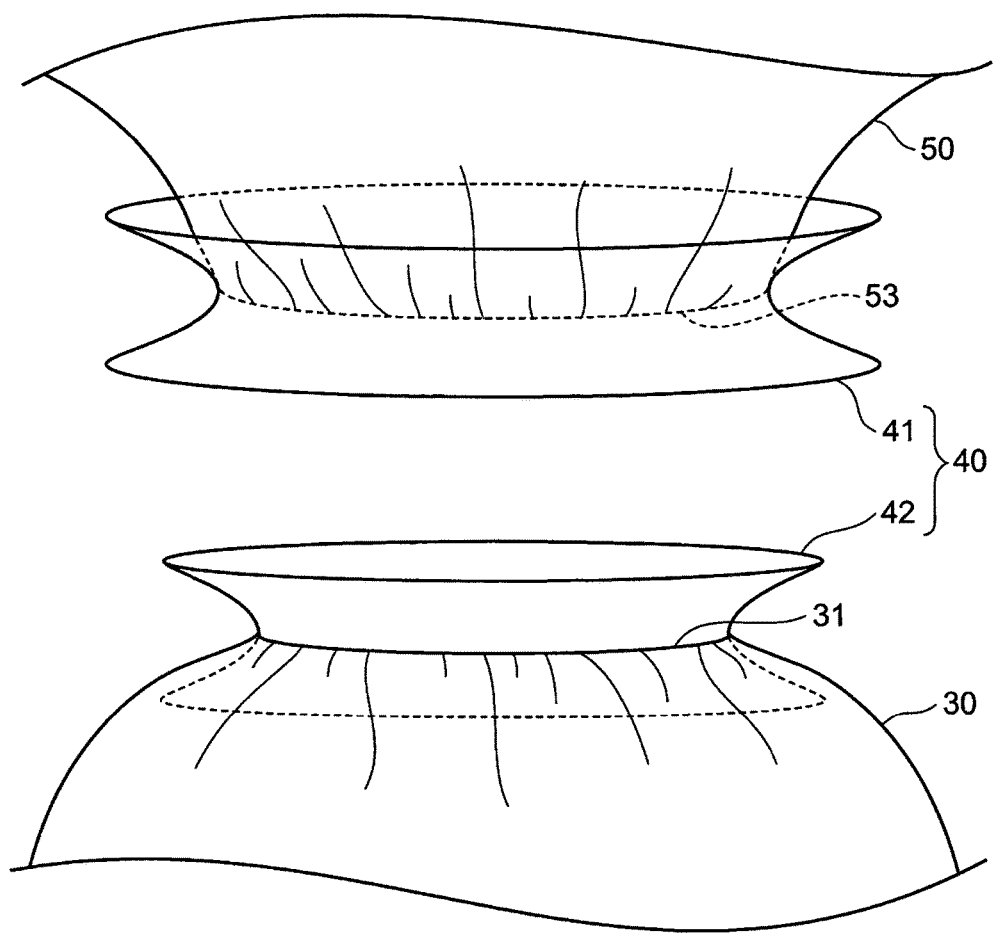

[Fig. 6]
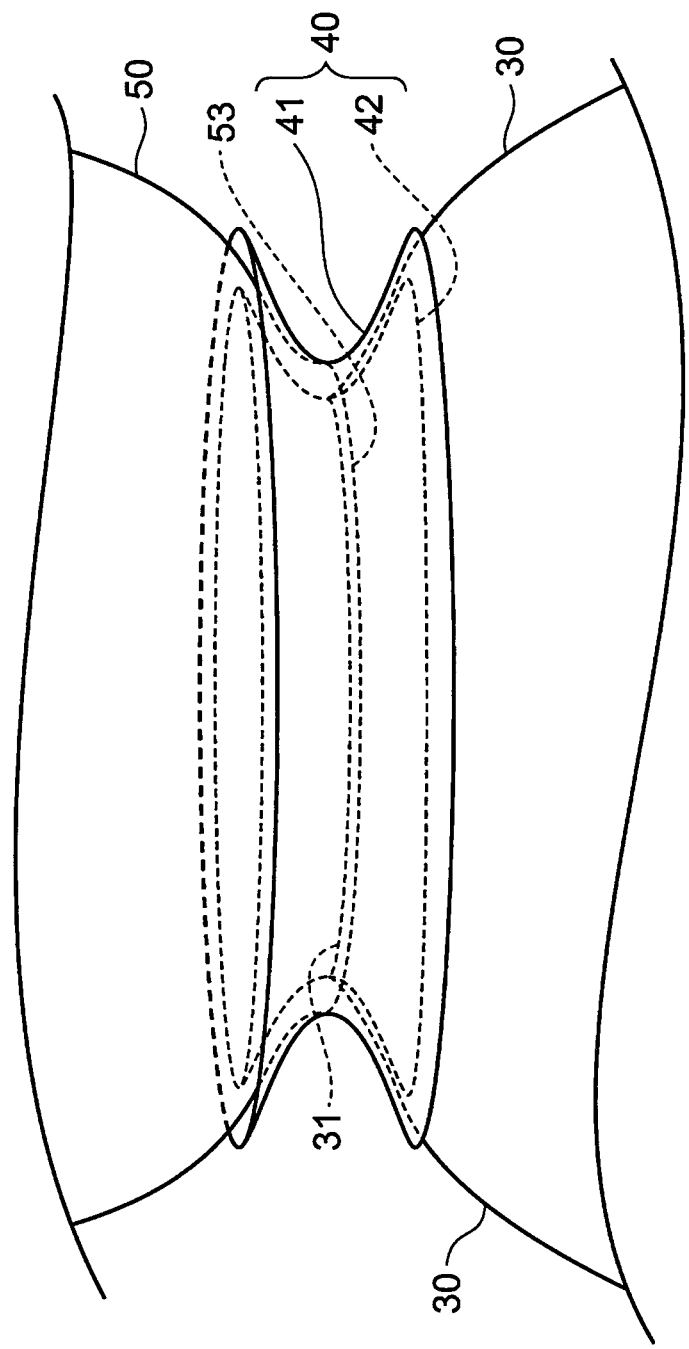

[Fig. 7]
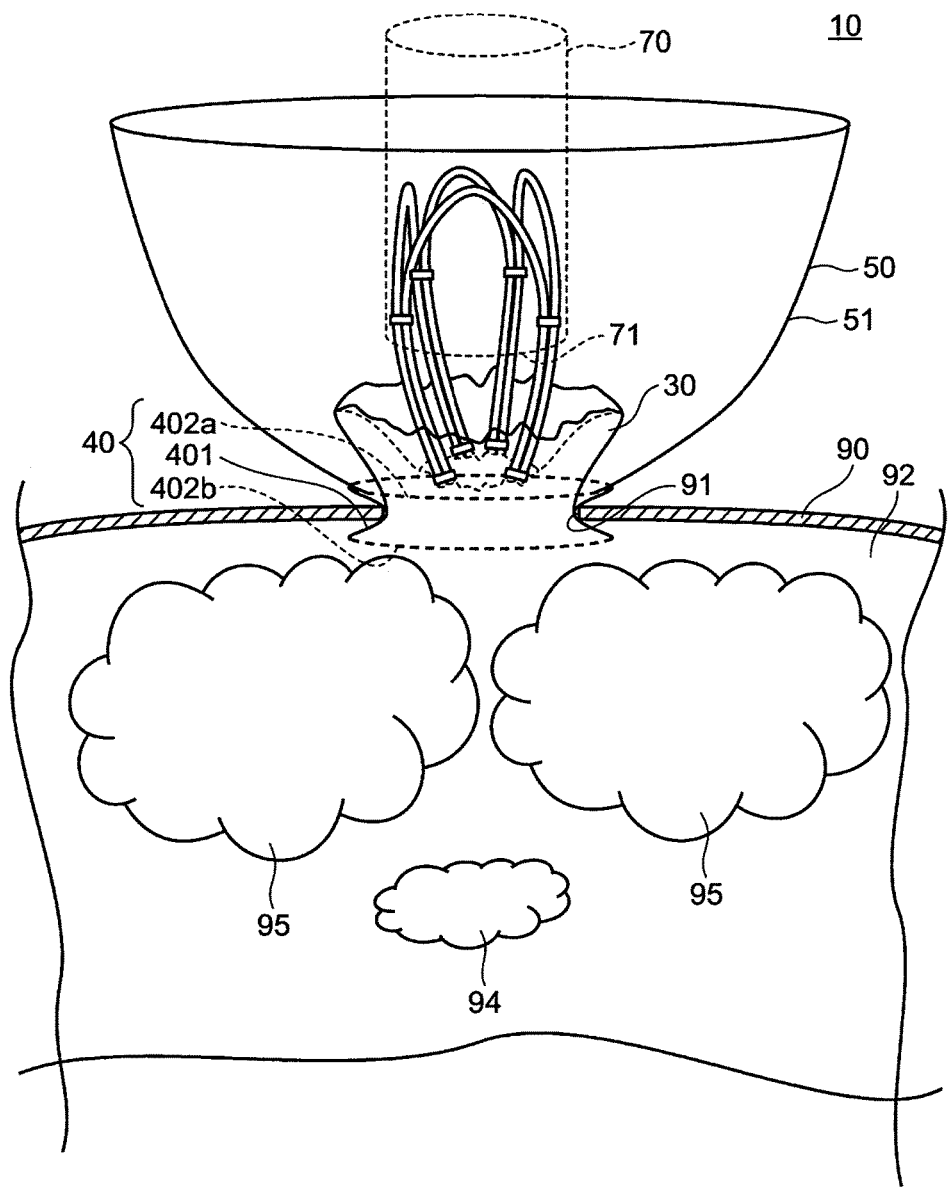

[Fig. 8]
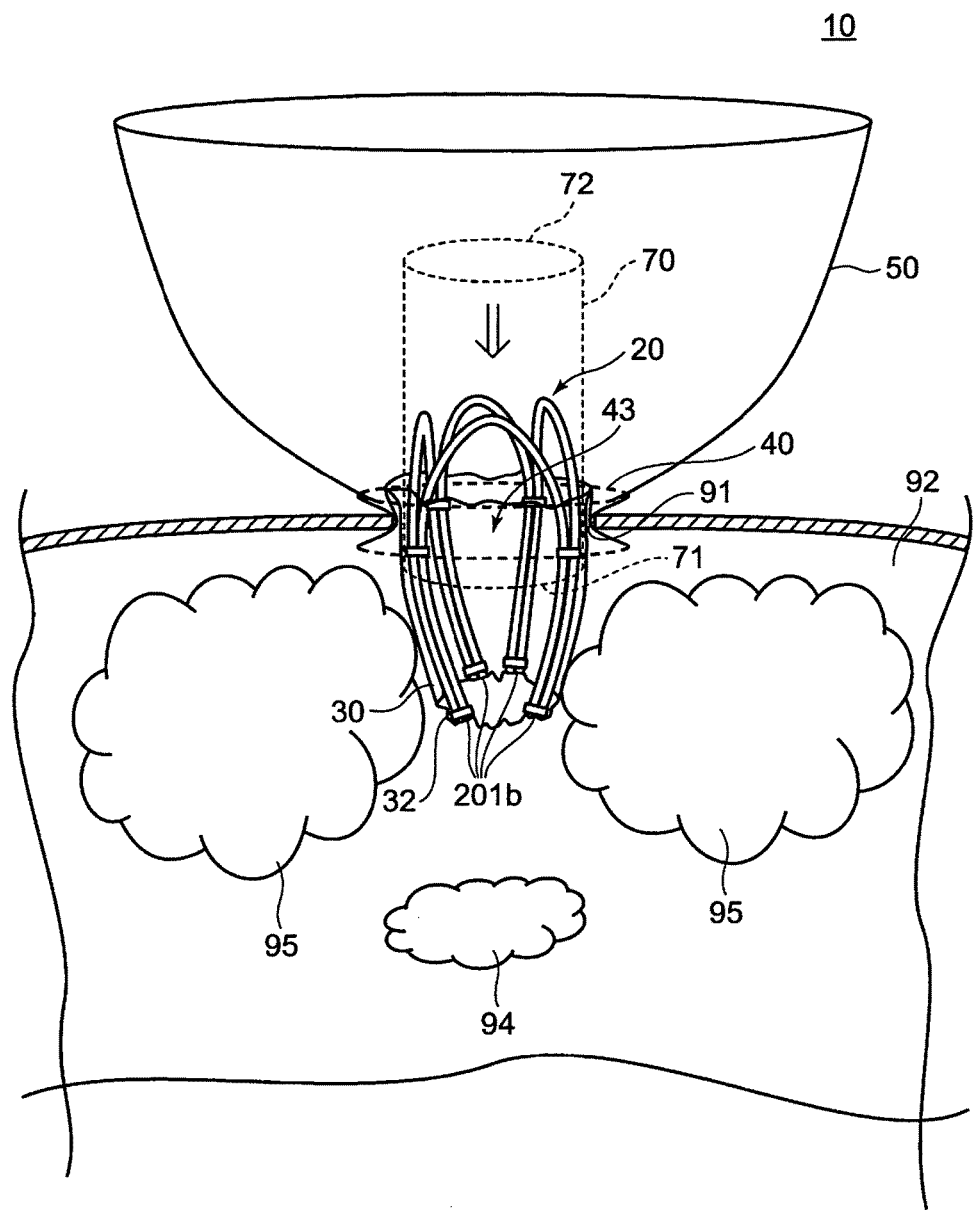

[Fig. 9]
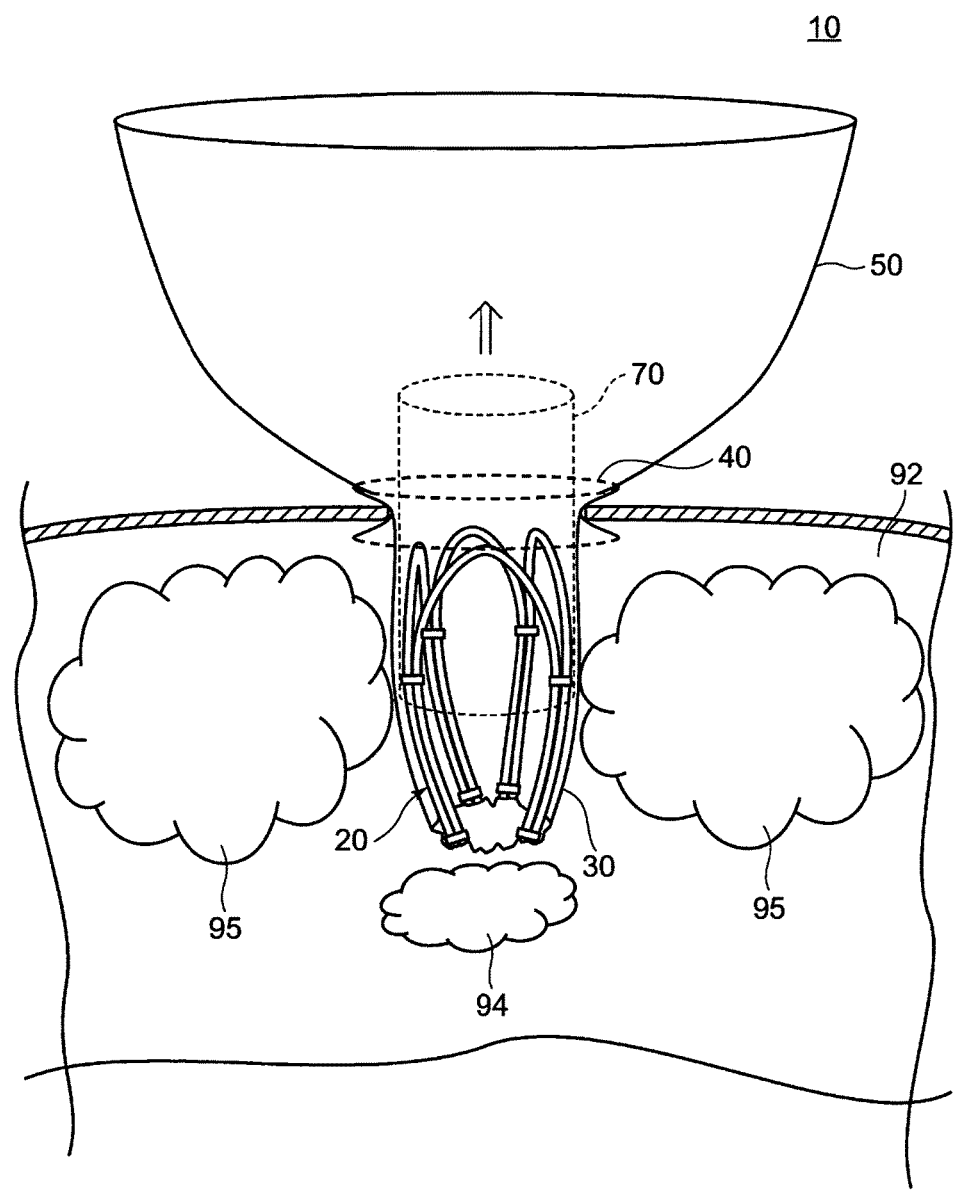

[Fig. 10]
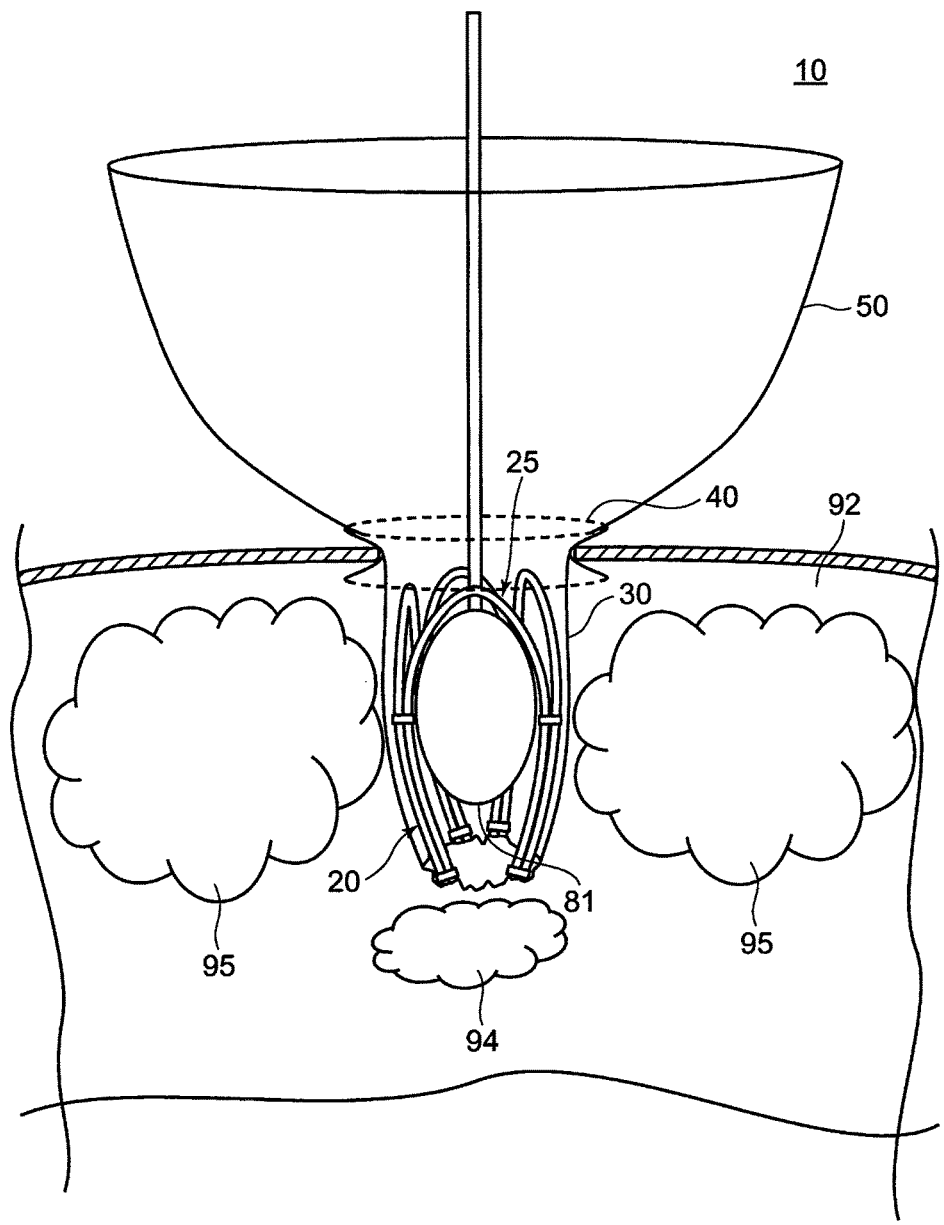

[Fig. 11]
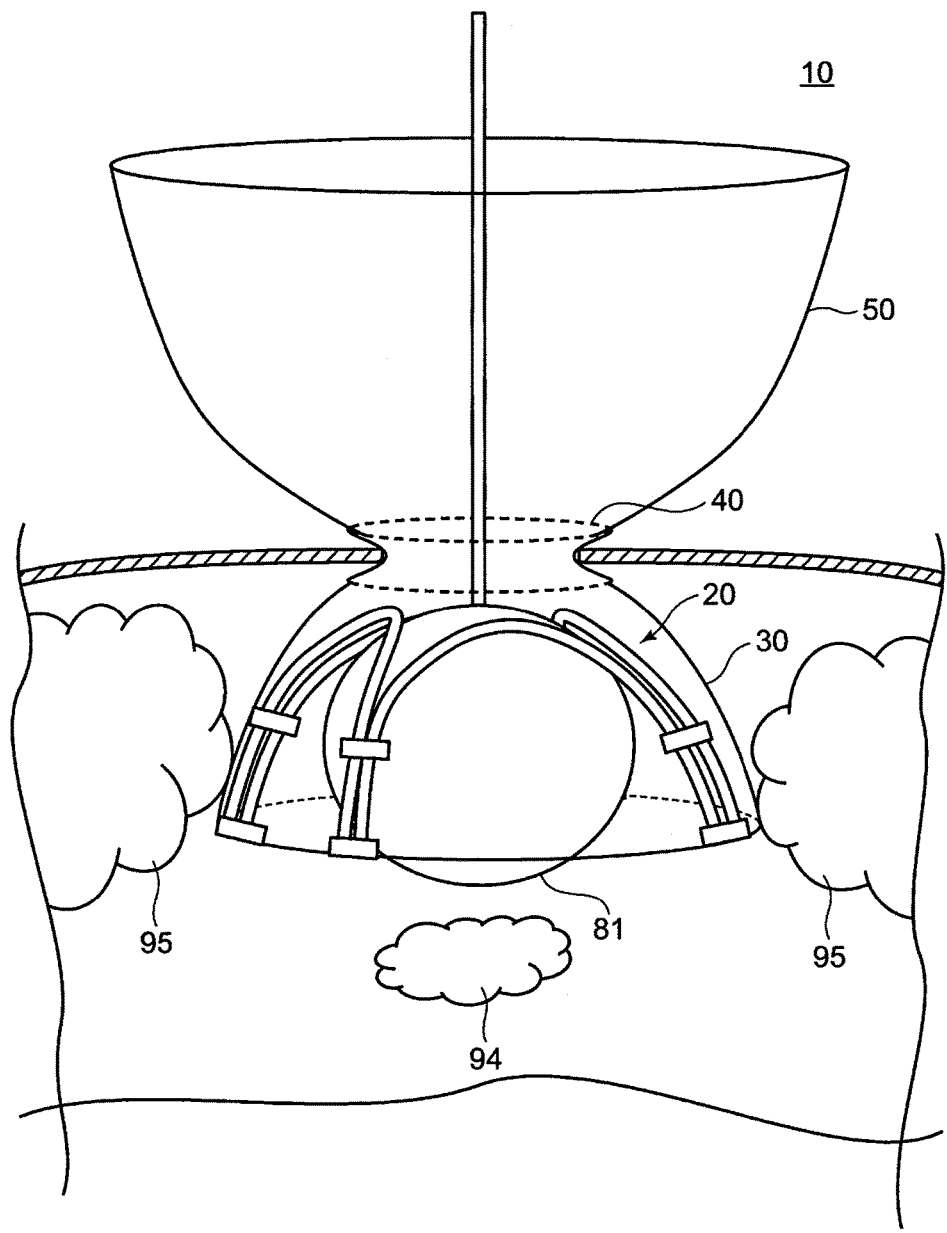

[Fig. 12]
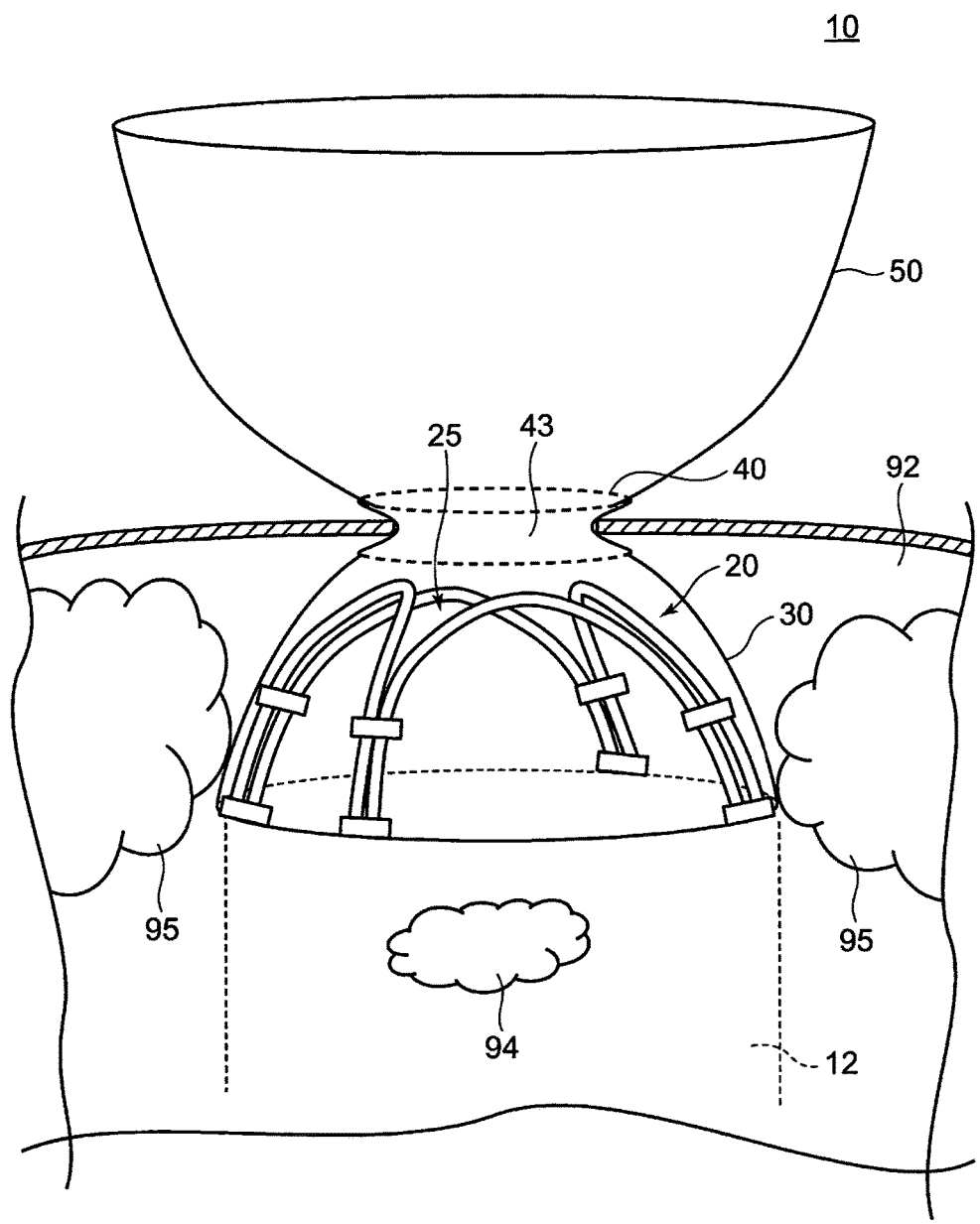

[Fig. 13]
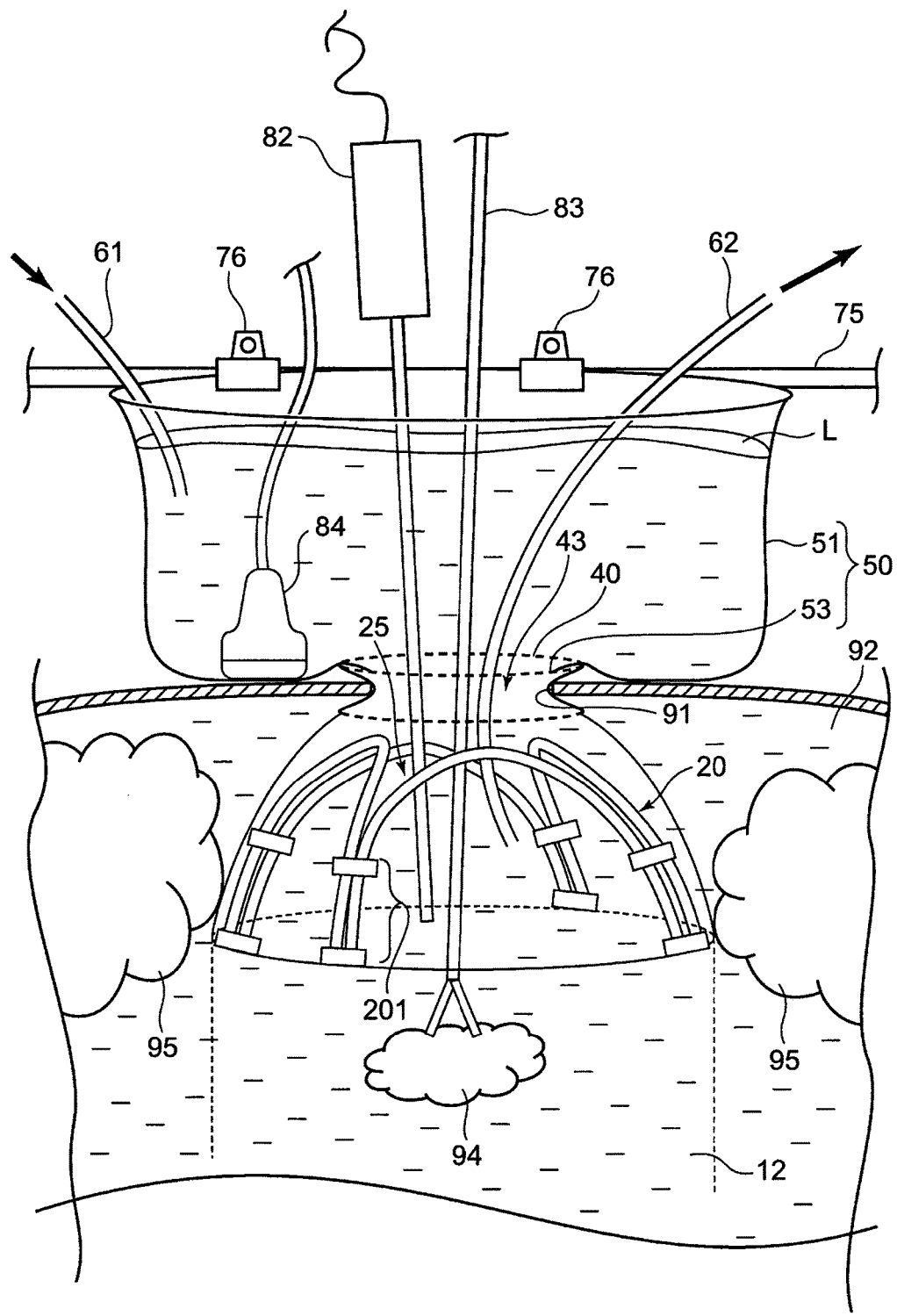

[Fig. 14]
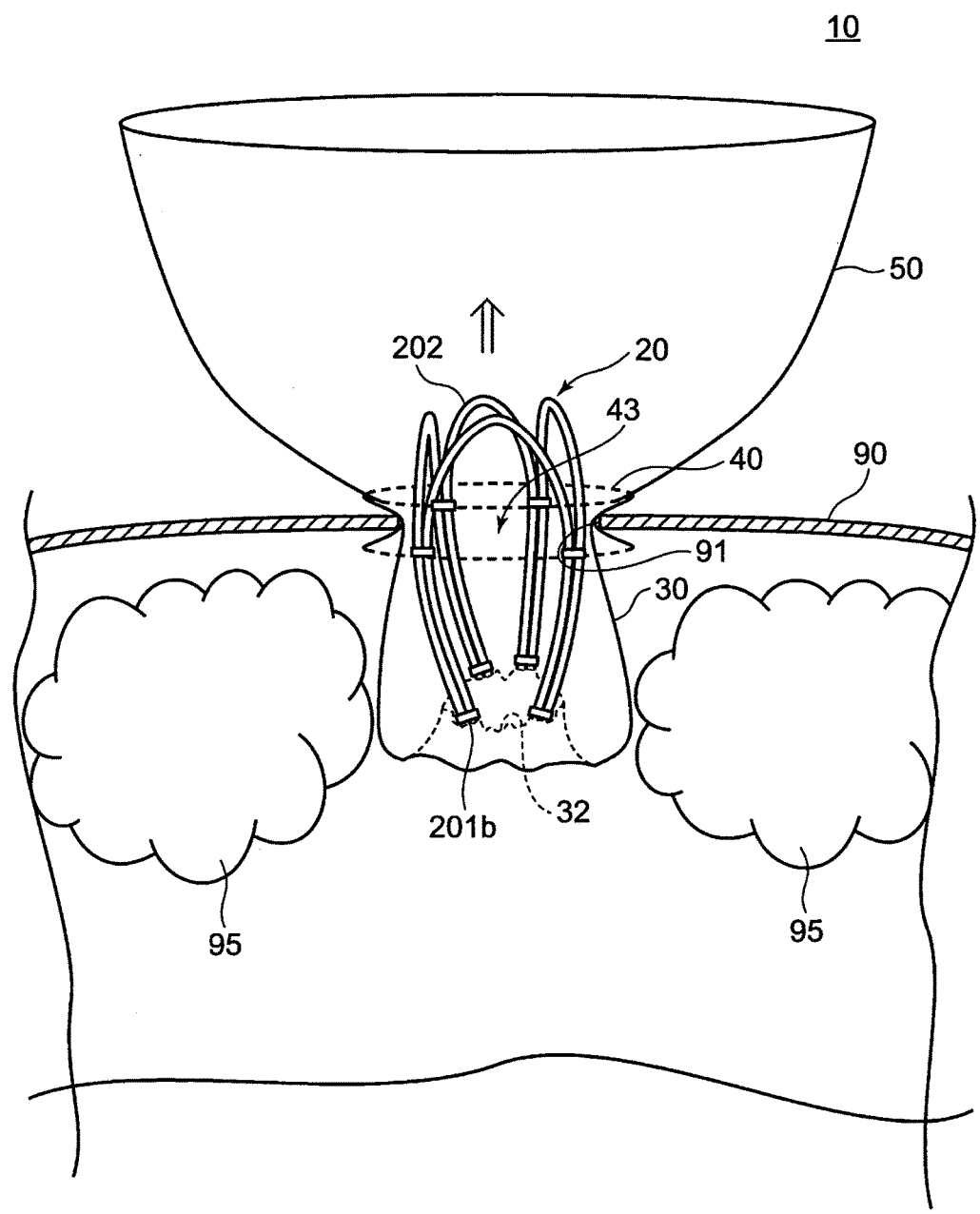

[Fig. 15]
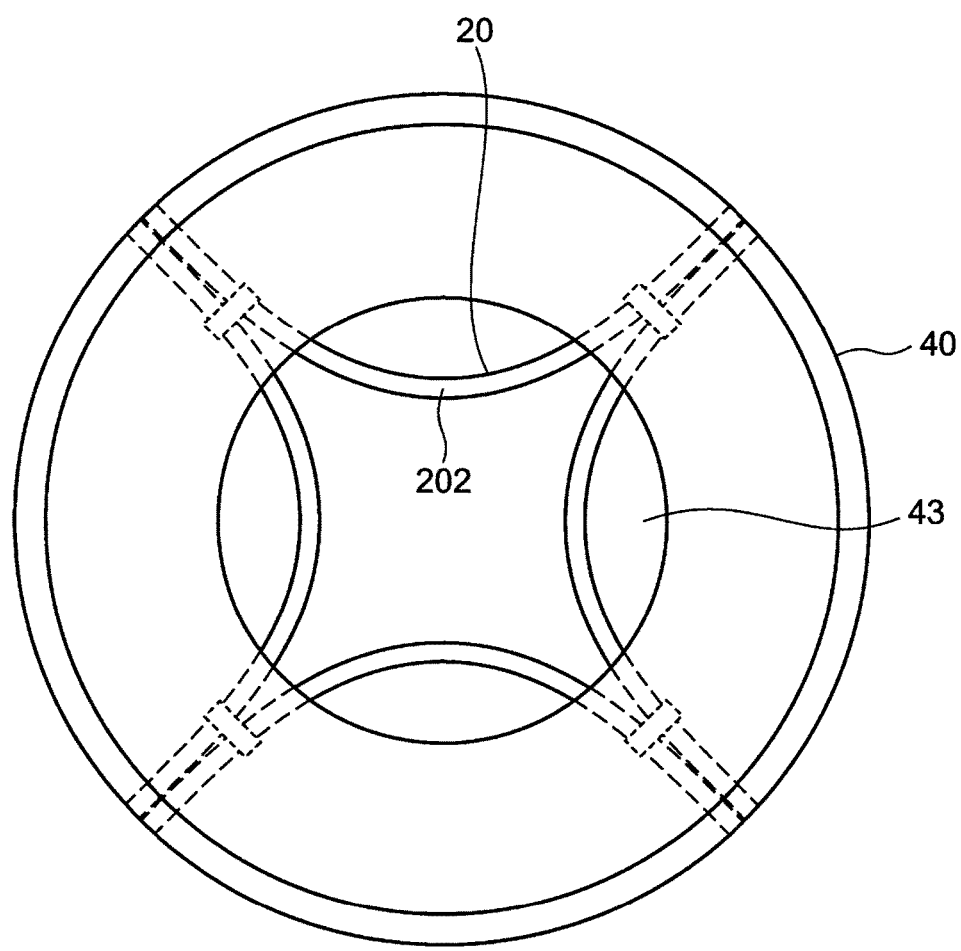

[Fig. 16]
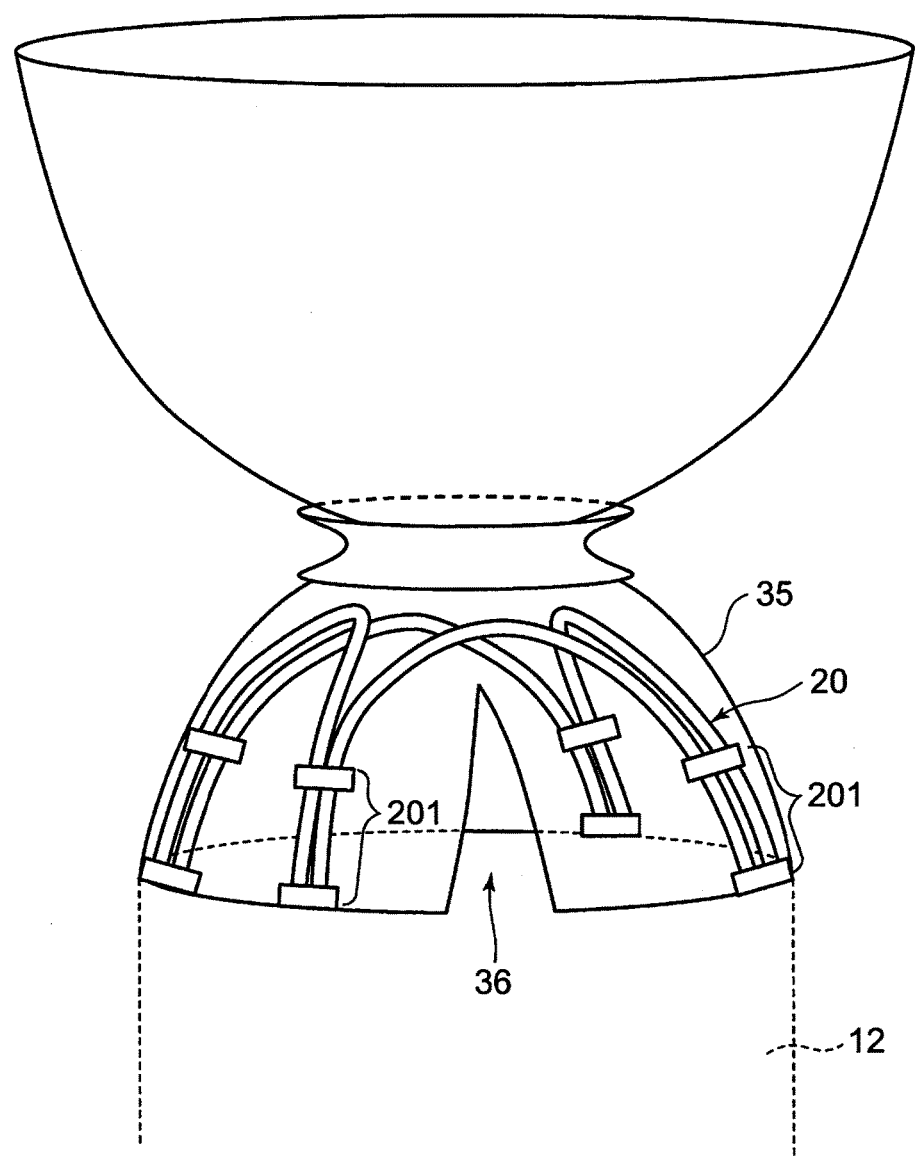

[Fig. 17]
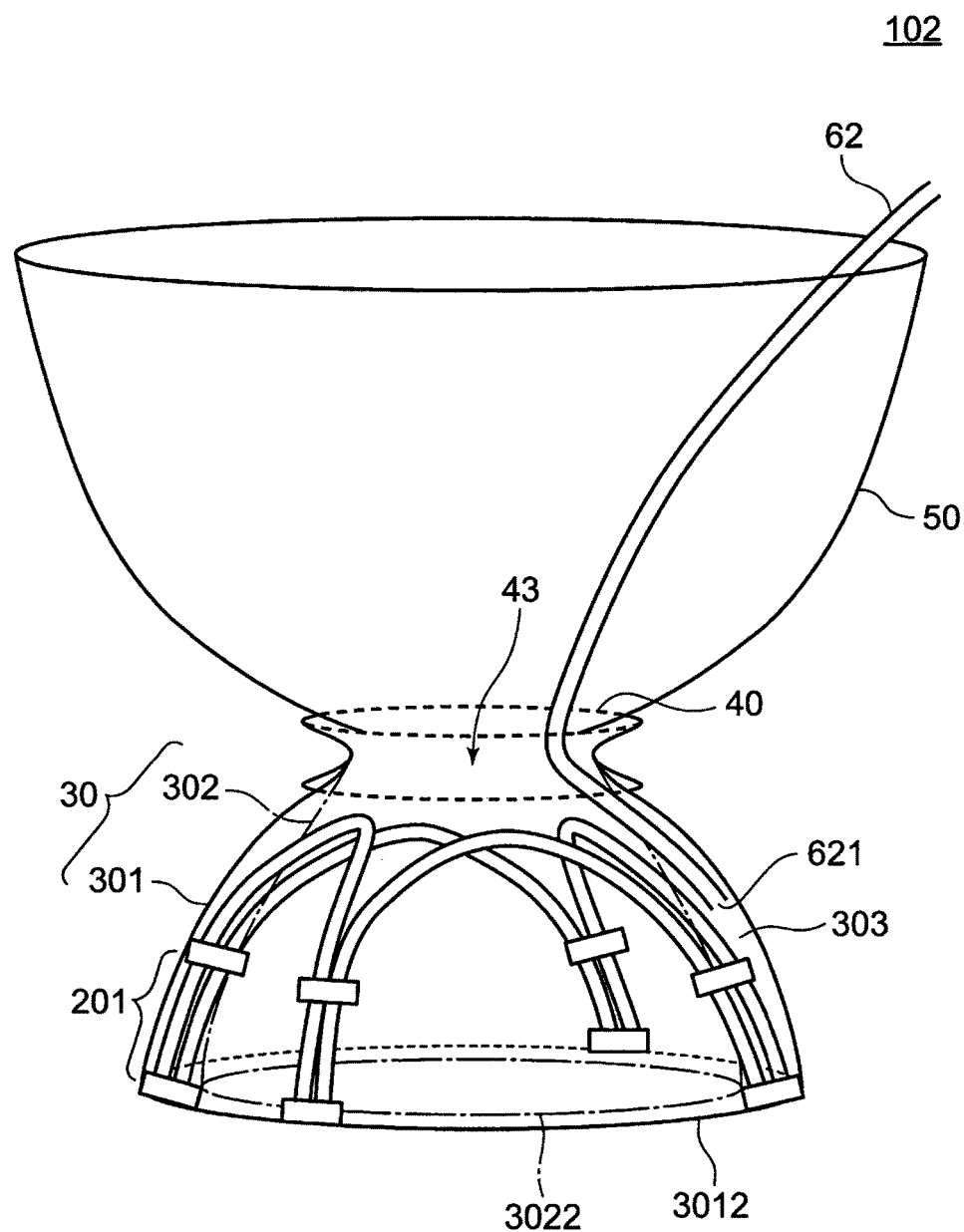

[Fig. 18]
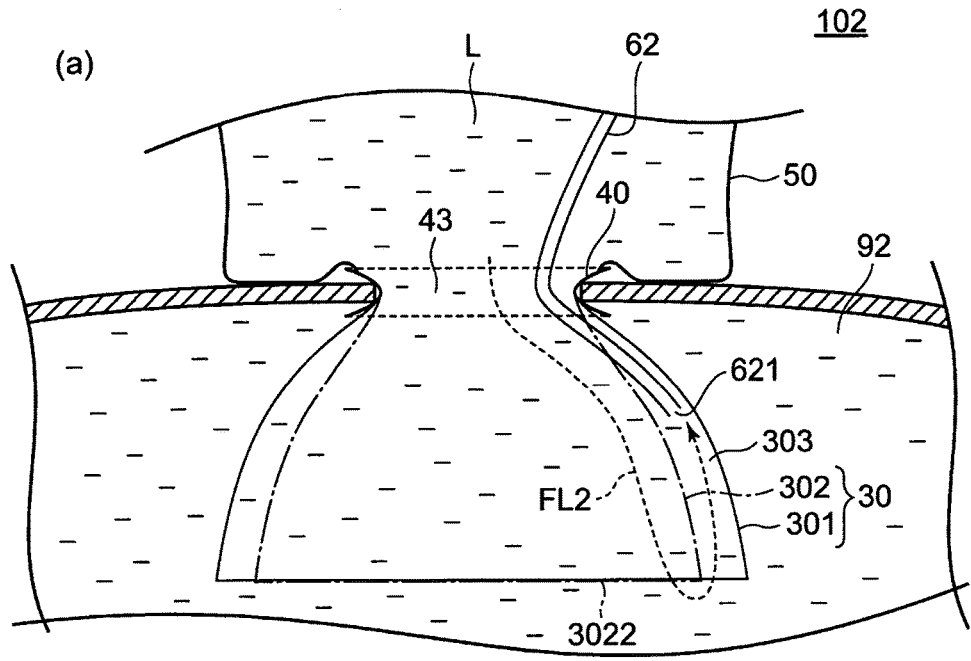
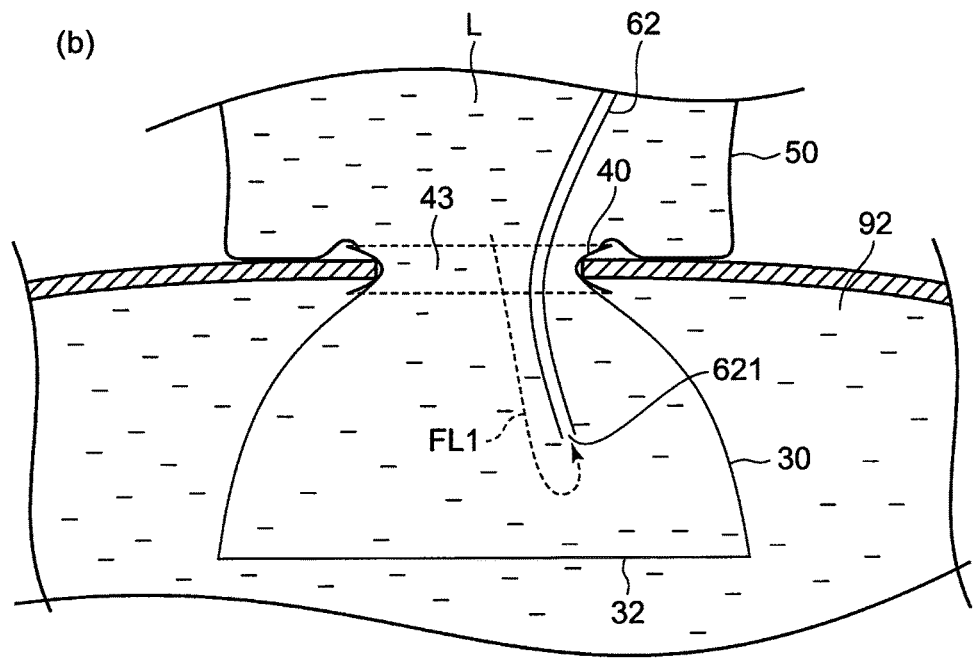

OPERATION FIELD-SECURING DEVICE

TECHNICAL FIELD

The present invention relates to an operation field-securing device that prevents surgical obstructions from invading an operation field in an endoscopic operation, and more particularly, to an operation field-securing device suitable for use during an underwater operation.

BACKGROUND ART

Conventionally, there has widely been known operational procedure (endoscopic operation) that carries out the operation through inserting a surgical instrument, such as an endoscope or electric scalpel, into a body cavity of a patient. When performing the operation procedure, organs other than the organ to be operated on and a greater omentum (which are hereinafter referred to "surgical obstruction") are desirably moved to the outside of the operation field. In recent years, operations have been proposed to be performed under an endoscopic view by filling a body cavity with a liquid, such as a normal saline solution (so-called "underwater operation", see, e.g., Non-Patent Documents 1 and 2). Under such an operational procedure, a surgical obstruction floats in the liquid and is thereby more likely to invade an operation field or area during the operation. Therefore, a device is required to prevent surgical obstructions from invading the operation field during the operation.

Patent Document 1 discloses an operation field-securing device as a device that prevents surgical obstructions from invading the operation field. The operation field-securing device includes a main body that has a plurality of wire rods arranged at intervals to form a truncated cone shape. The main body is designed to vary its maximum diameter by changing at least one of the posture and shape of the wire rods.

Patent Document 2 discloses a self-expanding deployment aid (retractor) for deployment of a field of view to clearly show the internal structure of the heart, such as that of a valve, during the operation of the heart. The retractor is configured from a cylindrical portion formed by spirally winding a soft pipe-shaped member. When operating on the heart, the retractor is placed within the heart to form a space in the heart, hence making it possible to secure a favorable field of view.

Patent Document 3 discloses an operation field-securing member that includes a pouch expandable by introducing a fluid thereinto and formed as an annular member when being expanded. The operation field-securing member is designed to secure an operation field inside the annular member, within a body cavity. The annular member is partially provided with penetration parts that communicate between the inside and outside of the annular member.

Patent Document 4 discloses a water tank for use in the underwater operation. The water tank includes a water-tank main body set in contact with a body wall and in which a liquid supplied into the body cavity is stored, and a through-hole formed at the bottom of the water-tank main body, the through-hole causing the liquid stored in the water-tank main body to flow into the body cavity via an incision made in the body wall. The water tank further includes a coupling member that liquid-tightly couples the water-tank main body with at least one area of the body wall and a retractor attached to the incision.

PRIOR ART DOCUMENT

Patent Document

Patent Document 1: JP 2014-61133 A
Patent Document 2: JP 2013-121478 A
Patent Document 3: JP 2008-284255 A
Patent Document 4: JP 2014-61132 A

Non-Patent Document

Non-Patent Document 1: T. Igarashi, Y. Shimomura, T. Yamaguchi, H. Kawahira, H. Makino, W. Yu, and Y. Naya, "Water-filled laparo-endoscopic surgery (WAFLES): feasibility study in porcine model," Journal of Laparoendoscopic & Advanced Surgical Techniques A, vol. 22, pp. 70-5, 2012.
Non-Patent Document 2: T. Igarashi, M. Teranuma, and T. Ishii, "Water-filled laparo-endoscopic surgery (WAFLES): A new surgical system performed under irrigation of isotonic water," Journal of Medical Imaging and Health Informatics, vol. 3, pp. 59-64, 2013

SUMMARY OF THE INVENTION

Problems to be Solved by the Invention

In keeping with the progress through minimally invasive operations, the size of an incision formed in the body has been decreased significantly. For this reason, an operation field-securing device is required to be insertable via a smaller incision into the body cavity, to be easily deployed within the body cavity, and to be readily removed from the incision to the outside of the body cavity.

Accordingly, it is an object of the present invention to provide an operation field-securing device that can be inserted into the body cavity, deployed within the body cavity, and removed to the outside of the body cavity with ease.

Means for Solving the Problems

An operation field-securing device according to the present invention is provided to secure an operation field by being deployed in a body cavity, the operation field-securing device including: at least three elongated parts extending radially in a deployed state; and curved parts, the number of which is the same as that of the elongated parts, in which each pair of the two adjacent elongated parts is connected at one ends thereof by the curved part, each of the curved parts is convex toward a side opposite to the elongated part, the curved parts are arranged circumferentially in the deployed state, and by deforming the curved parts, the operation field-securing device is capable of being brought into either one of a contracted state where a distance between the adjacent elongated parts is shortened and the deployed state where the distance between the adjacent elongated parts is expanded.

The operation field-securing device in the present invention includes three or more of the elongated parts and the curved parts connecting these elongated parts, thereby holding surgical obstructions that would otherwise invade the field (operation field) enclosed by the elongated parts, outside the operation field in the deployed state. When placing the operation field-securing device in the body cavity, the curved parts are positioned in the vicinity of the incision formed in the body, and thereby a region enclosed by the curved parts serves as an insertion port through which a surgical instrument, such as an endoscope, is inserted into the operation field during the operation.

The operation field-securing device according to the present invention is configured such that the elongated parts are connected together by the curved parts, whereby the operation field-securing device can be formed in an elongated shape by compressing and deforming the curved part (in the contracted state). Thus, the operation field-securing device can be easily inserted into the body cavity even through the small incision.

After inserting the operation field-securing device into the body cavity, a general organ displacing balloon for use in the endoscopic operation is inserted into and inflated in a space enclosed by the elongated parts to thereby deform the curved parts, which makes it possible to easily deploy the operation field-securing device.

When removing the operation field-securing device from the body cavity, the curved parts positioned in the vicinity of the incision are compressed and deformed, so that the operation field-securing device can be simply transformed from the deployed state into the contracted state. Only by pulling the operation field-securing device in the contracted state toward the outside of the body, the operation field-securing device can be easily removed from the body cavity.

Effects of the Invention

The operation field-securing device according to the present invention can be inserted into the body cavity, deployed within the body cavity, and removed to the outside of the body cavity with ease.

BRIEF DESCRIPTION OF THE DRAWINGS

FIG. 1 is a schematic perspective view of an operation field-securing device according to a first embodiment.

FIGS. 2(a) and 2(b) are schematic perspective views of a framed structure used in the operation field-securing device according to the first embodiment, in which FIG. 2(a) shows a deployed state, and FIG. 2(b) shows a contracted state.

FIG. 3 is a schematic top view showing the framed structure in the deployed state.

FIG. 4 is a schematic perspective view of an annular member used in the operation field-securing device according to the first embodiment.

FIG. 5 is a schematic partially enlarged view of an operation field-securing device using two annular members.

FIG. 6 is a schematic partially enlarged view showing a state of a combination of the two annular members shown in FIG. 5.

FIG. 7 is a schematic perspective view for explaining a method of using the operation field-securing device according to the first embodiment.

FIG. 8 is a schematic perspective view for explaining the method of using the operation field-securing device according to the first embodiment.

FIG. 9 is a schematic perspective view for explaining the method of using the operation field-securing device according to the first embodiment.

FIG. 10 is a schematic perspective view for explaining the method of using the operation field-securing device according to the first embodiment.

FIG. 11 is a schematic perspective view for explaining the method of using the operation field-securing device according to the first embodiment.

FIG. 12 is a schematic perspective view for explaining the method of using the operation field-securing device according to the first embodiment.

FIG. 13 is a schematic perspective view for explaining the method of using the operation field-securing device according to the first embodiment.

FIG. 14 is a schematic perspective view for explaining the method of using the operation field-securing device according to the first embodiment.

FIG. 15 is a schematic top view of the annular member and a part of a framed structure 20 exposed from an opening of the annular member.

FIG. 16 is a schematic perspective view of an operation field-securing device according to a first modified embodiment.

FIG. 17 is a schematic perspective view of an operation field-securing device according to a second modified embodiment.

FIG. 18(a) is a schematic partial front view for explaining the flow of perfusate in the operation field-securing device according to the first embodiment, and FIG. 18(b) is a schematic partially front view for explaining the flow of perfusate in the operation field-securing device according to the second modified embodiment.

EMBODIMENTS FOR CARRYING OUT THE INVENTION

Embodiments of the present invention will be described in detail below with reference to the accompanying drawings. In the description below, the terms indicative of specific directions or positions (e.g., "upper", "lower", "right", "left", and other words including these words) are used as appropriate. The use of these terms is to make the understanding of the present invention easy with reference to the drawings, and does not limit the technical scope of the present invention by their meanings. The parts indicated with the same reference characters represented in a plurality of the drawings denote the same parts or members.

First Embodiment

An operation field-securing device in this embodiment is used to secure an operation field in an endoscopic operation. The operation field-securing device 10 shown in FIG. 1 includes a framed structure 20 composed of four tubes 21 to 24. The operation field-securing device 10 may further include a sheet member 30 which covers the framed structure 20, an annular member 40 to which the sheet member 30 is attached, and a water storage member 50 which is connected to the annular member 40. When using the operation field-securing device 10, the annular member 40 is placed onto an incision formed in the body, the framed structure 20 and the sheet member 30 are disposed in the body cavity, and the water storage member 50 is disposed outside the body.

The respective components of the operation field-securing device 10 will be described in detail below.

As shown in FIGS. 2 to 3, the framed structure 20 of this embodiment is configured such that the respective four tubes 21 to 24 are connected together while each being bent in an arc shape. The tubes 21 to 24 in use are preferably elastic tubes. The term "elastic tube" as used in the present description means a tube that is characterized to be bent and warped away from its long axis when a load is applied to the tube and then restored elastically to its original shape when the load is removed.

Note that the tubes 21 to 24 in use may also be plastically deformable tubes, in addition to the elastic tubes. Further, instead of the tubes 21 to 24, solid elongated members that are elastically deformable or plastically deformable can also be used.

In this embodiment, the framed structure 20 using the elastic tubes as the tubes 21 to 24 will be described below by way of Example.

As shown in FIG. 2(a), the elastic tubes 21 to 24 include curved elements 212, 222, 232 and 242, each located at the center of the corresponding elastic tube in its longitudinal direction, first elongated elements 211, 221, 231 and 241, each positioned on one end of each curved element, and second elongated elements 213, 223, 233 and 243, each positioned on the other end of each curved element. The elastic tubes 21 to 24 are arranged circumferentially such that the curved parts 202 (curved elements 212, 222, 232 and 242) are convex upward. The first elongated element of each elastic tube is bonded in parallel with the second elongated element of the adjacent elastic tube, while the second elongated element of each elastic tube is bonded in parallel with the first elongated element of the elastic tube adjacent on the opposite side. For example, the first elongated element 211 of the elastic tube 21 is bonded with the second elongated element 223 of the adjacent elastic tube 22, while the second elongated element 213 of the elastic tube 21 is bonded with the first elongated element 241 of the elastic tube 24 adjacent on the opposite side. A pair of the bonded elongated elements (for example, the first elongated element 211 and the second elongated element 223) configures a single elongated part 201. The pair of elongated elements can be fixed to each other using fixing a member 26 such as a binding band. Instead of using the fixing member 26, the pair of elongated elements may be fixed to each other by an adhesion or welding It can be interpreted that in the framed structure 20 configured in this way, each pair of the two adjacent elongated parts 201 (first elongated elements 211, 221, 231, 241 and second elongated elements 213, 223, 233, 243) is connected with their one ends (upper ends) 201a by the curved part 202 (see FIG. 2(a) and FIG. 3). Each of the curved parts 202 is convex toward the side opposite to the direction (downward direction) in which the elongated part 201 is connected, in other words, convex upward.

In the connection relationship between each elongated element and the curved part, one end (upper end) of one of a pair of elongated elements configuring one elongated part 201 is connected to one end of the curved part 202, while one end (upper end) of the other elongated element is connected to the other end of another curved part 202. When specifically explaining with reference to FIG. 2(a), in the elongated part 201 configured of the pair of elongated elements 211 and 223, the upper end of the right-side elongated element 211 is connected to the left end of the curved element 212, while the upper end of the left-side elongated element 223 is connected to the right end of another curved element 222.

The curved element (for example, curved element 212) and the two elongated elements (for example, elongated elements 211 and 213) connected to both ends of the curved element are preferably configured of one elastic tube (elastic tube 21).

Note that although in this embodiment, one elongated part 201 is configured of two elongated elements as shown by way of example, one elongated part 201 can be formed of one elongated element.

FIGS. 2(a) and 3 show the framed structure 20 in its deployed state. The term "deployed state" as used in the present description means a state where the framed structure 20 expands downward to form a domed shape, which is similar to a state where an umbrella expands its frames. As can be seen from FIG. 3, in the deployed state, the curved parts 202 of the framed structure 20 are arranged circumferentially, and the elongated parts 201 are extended radially.

The term "radially" as used in the present description indicates the state of expanding outward from one point. The elongated parts 201 shown in FIG. 2(a) expand obliquely downward while being slightly curved. Note that the elongated parts 201 may expand substantially in the horizontal direction.

FIG. 2(b) shows the framed structure 20 in the contracted state. The term "contracted state" as used in the present description means a state where the curved parts 202 are compressed and deformed (that is, deformed to be more curved) to make adjacent elongated parts 201 close to each other, thereby shortening a distance between these elongated parts. To obtain such a contracted state, it is necessary to exert a force to make the curved parts 202 more curved. For example, the force is exerted inward from the outer side on the whole four curved parts 202 or the whole four elongated parts 201.

Since this embodiment employs the elastic tubes 21 to 24, a repulsive force to restore the curved parts to the original shape becomes significant when the degree of curve of the curved parts 202 is set large (that is, when the elastic tubes 21 to 24 are significantly warped from the long axis of each of the elastic tubes 21 to 24). Thus, when the force exerted to bring the framed structure into the contracted state is released, the shape of the curved part 202 intends to be recovered elastically to the original shape. That is, the framed structure 20 can change from the contracted state to the deployed state. In the deployed state, the distance between the elongated parts 201 is increased.

Note that the framed structure 20 can also be configured by using a plastically deformable member (for example, metal tube, metal wire, resin-coated metal wire and the like) instead of the elastic tubes. In such a case, even when the curved parts 202 are compressed and deformed, no repulsive force is generated in the curved parts 202. Thus, the curved parts 202 are deformed to expand (or extend), so that the framed structure 20 can be changed from the contracted state to the deployed state.

The framed structure 20 is configured by integrating the elongated parts 201 and the curved parts 202. The framed structure 20 has a simple structure and thereby can be manufactured at relatively low cost. The deformation of the framed structure 20 between the contracted state and the deployed state can be performed only by deforming the curved parts 202, so that the operation of the framed structure 20 can be easily performed.

Note that the elongated parts 201 define the operation field and serve to eliminate surgical obstruction from the operation field. Thus, at least three, for example, three to ten, and preferably four to six elongated parts 201 can be used. As can be seen from FIG. 3, the curved parts 202, the number of which is the same as that of the elongated parts 201, are needed in order to connect the elongated parts 201 in a ring shape.

Referring to FIG. 1 again, at least the elongated parts 201 of the framed structure 20, preferably, the entire framed structure 20 including the curved parts 202, may be preferably covered with the sheet member 30. The sheet member 30 covers a space between the elongated parts 201 of the framed structure 20, which can prevent the surgical obstructions 95 from entering the operation field via the space between the adjacent elongated parts 201.

The sheet member 30 is preferably formed of a readily deformable sheet material such that the sheet member is positioned adjacent to the periphery of the framed structure 20 when it is in the contracted state, and such that the sheet member can follow the deformation of the framed structure 20 when it is deformed from the contracted state to the deployed state. For example, the sheet member 30 can be formed of a soft sheet material with flexibility. The soft sheet material can be a sheet material made of a resin, such as polyvinyl chloride or silicone. In particular, the sheet member 30 is preferably a transparent sheet material because the state of the displaced surgical obstructions 95 can be recognized during the operation.

The sheet member 30 can be fixed to the framed structure 20 and the annular member 40. In particular, preferably, an upper edge part (first edge part) of the sheet member 30 is attached to the annular member 40, while a lower edge part (second edge part) 32 of the sheet member 30 is attached to the lower ends (other ends) 201b of the elongated parts 201 in the framed structure 20. That is, the framed structure 20 is indirectly fixed to the annular member 40 via the sheet member 30, so that the framed structure 20 can be moved relatively freely with respect to the annular member 40. For example, the framed structure 20 is deformed in the contracted state, so that the framed structure 20 can pass through the inside (opening 43) of the annular member 40 from one side to the other side thereof (from a lower side to an upper side of the annular member 40, or from an upper side to a lower side thereof).

Note that since the sheet member 30 is fixed to lower ends 201b of the elongated parts 201, the sheet member 30 also moves together with the movement of the framed structure 20. For example, when the framed structure 20 is disposed under the annular member 40, the sheet member 30 is also disposed under the annular member 40. In contrast, when the framed structure 20 is disposed above the annular member 40, the sheet member 30 is also disposed above the annular member 40.

Means for fixing the sheet member 30 to the elongated parts 201 may be any means that is not detached when transforming operation of the framed structure 20 from the contracted state to the deployed state and that is safe during use within a living body. Examples of the fixing means can include an adhesion using a safe adhesive for the living body, a suture using a suture thread or the like, mechanical fixing using a fixing tool, fixing by heat welding and the like. Referring to FIG. 1, the lower edge part 32 of the sheet member 30 is also fixed to the elongated parts 201 by fixing members 26, each of which is used to fix the pair of elongated elements in the framed structure 20 to each other so as to configure the elongated part 201.

The annular member 40 can be used as a device (so-called annular retractor) that is fitted into an incision 91 to secure the access to the inside of a body cavity 92. By fixing the annular member 40 to the incision 91, the operation field-securing device 10 can be fixed to the body of a patient.

The annular member 40 is preferably, for example, a retractor (retractor made of silicone) as shown in FIG. 4. The annular member 40 (retractor) is configured by holding ends of a cylindrical silicone rubber sheet 401 by elastic rings 402a and 402b. As the silicone rubber sheet 401, a thin medical sheet with excellent elasticity is used. The elastic rings 402a and 402b each have a substantially exact circle and can be deformed easily by exerting a force with a hand. When releasing the force, the elastic rings are elastically restored into the substantially exact circle shape. In the retractor, the lower elastic ring 402b is disposed in the body, and the upper elastic ring 402a is disposed outside the body. The retractor is to press and expand the incision 91 in a circle shape by the outer surface of the silicone rubber sheet 401. The operation is performed through an opening 43 of the retractor.

The operation field-securing device 10 can be used for the underwater operation. The underwater operation is performed while the body cavity is filled with liquid, such as a normal saline solution. If the liquid becomes turbid due to bleeding or the like, it is difficult to identify the operation field. Thus, the liquid is desirably perfused constantly. The perfused liquid (hereinafter referred to as a "perfusate") is supplied from an injection pipe and emitted from a suction pipe. When the injection pipe is set in the body cavity, a turbulent flow tends to occur in the perfusate within the body cavity, which might promote the turbidity of the perfusate due to bleeding. Thus, to suppress the turbulent flow of the perfusate in the body cavity, the operation field-securing device 10 is desirably provided with the water storage member 50 for temporarily storing the perfusate supplied from the injection pipe (FIG. 1).

As shown in FIG. 1, the water storage member 50 includes a main body 51 for storing a liquid and a communication port 53 provided at a lower part of the main body. The communication port 53 is water-tightly connected to the retractor used as the annular member 40. The retractor (for example, retractor made of silicone) can be fixed in intimate contact with the incision provided in the body wall, thereby making it possible to prevent the perfusate from leaking between the incision and the retractor. The communication port 53 of the water storage member 50 is water-tightly fixed to the retractor, thereby making it possible to prevent the perfusate from leaking between the retractor and the water storage member 50. Thus, there is little possibility that a surgical bed and a floor in an operating room are contaminated with perfusate containing blood during the underwater operation.

The water storage member 50 is preferably formed of a soft sheet. When the water storage member 50 stores therein the perfusate, the water storage member 50 is deformed by the weight of the perfusate to be brought into contact with the surface of the body located around the annular member 40. During the underwater operation, the adhesion at an interface between the incision and the annular member 40 is enhanced, and thus the effect of preventing the leakage of the perfusate from the interface can be expected. Note that if the water storage member 50 made of a soft sheet does not have enough rigidity to stand by itself, the water storage member 50 needs to be held by disposing a support member, such as a strut, above the patient and fixing the water storage member 50 to the support member.

When fixing the sheet member 30 and the water storage member 50 to the annular member 40, two annular members (first annular member 41 and second annular member 42) can be used as shown in FIGS. 5 and 6. The second annular member 42 is detachably fitted into an inside of the first annular member 41. Methods for attaching the sheet member 30 and the water storage member 50 using the two annular members 41 and 42 will be described individually.

As shown in FIG. 5, an upper edge part (first edge part) 31 of the sheet member 30 is attached to an outer surface of the second annular member 42. As shown in FIG. 6, the second annular member 42 is fitted into the inside of the first annular member 41, whereby the upper edge part 31 of the sheet member 30 is sandwiched between the first annular member 41 and the second annular member 42.

As to the water storage member 50, as shown in FIG. 5, the communication port 53 is attached to the inner surface of the first annular member 41. As shown in FIG. 6, the second annular member 42 is fitted into the inside of the first annular member 41, whereby the communication port 53 is sandwiched between the first annular member 41 and the second annular member 42.

The use of the two annular members 41 and 42 can sandwich the upper edge part 31 of the sheet member 30 and the communication port 53 of the water storage member 50 between these annular members. Consequently, the leakage of the liquid from the interface between the annular member 40 and the sheet member 30 and the leakage of the liquid from the interface between the annular member 40 and the water storage member 50 can be effectively prevented when performing the underwater operation.

When performing the operation using the operation field-securing device 10, in some cases, the framed structure 20 is preferably replaced with another one having a different size while the water storage member 50 is maintained. For example, there is a case in which a smaller or larger framed structure 20 than the framed structure 20 currently used is preferably used depending on the physique or operation part of a patient. In the operation field-securing device 10 having the annular members 41 and 42 as shown in FIG. 5, the water storage member 50 fixed to the first annular member 41 can be separated from the sheet member 30 fixed to the second annular member 42 (and the framed structure 20 fixed to the sheet member 30). Thus, to meet the needs of surgeons, the second annular member 42 is removed from the first annular member 41 first, and then "another second annular member 42" having the framed structure 20 with a different size is attached to the inside of the first annular member 41. In this way, the framed structure 20 can be replaced while the water storage member 50 is maintained.

Next, a method of using the operation field-securing device 10 according to this embodiment will be described with reference to FIGS. 7 to 14. Note that in FIGS. 7 to 14, to easily understand an operation state of the operation field-securing device 10, the annular member 40 is illustrated with a front half thereof removed. The removed part of the annular member 40 is indicated by a dashed line.

<1. Attachment to Incision>

As shown in FIG. 7, the incision 91 is formed in a body wall 90 by a scalpel or the like in the position that can access an organ to be isolated (operation target part 94). In an embodiment shown in FIG. 7, other organs (surgical obstructions 95) are present above the operation target part 94.

Then, the operation field-securing device 10 is fixed to the incision 91. Note that before fixing, the framed structure 20 and the sheet member 30 in the operation field-securing device 10 are accommodated in the main body 51 of the water storage member 50. The framed structure 20 is preferably in the contracted state. For example, a cylindrical member 70 with an outer diameter which is smaller than the inner diameter of the opening 43 in the annular member 40 is prepared. The curved parts 202 of the framed structure 20 are inserted into a lumen of the cylindrical member 70 from its one end 71, whereby the curved parts 202 are compressed and deformed. The use of the cylindrical member 70 makes it easy to hold the framed structure 20 in the contracted state. Note that not only the curved parts 202 of the framed structure 20, but also a part or all of the elongated parts 201 may be inserted into the cylindrical member 70.

To fix the operation field-securing device 10, the annular member 40 is fixed to the incision 91. When the annular member 40 is a silicone incision (see FIG. 4), the lower elastic ring 402*b* is deformed first into an elongated shape with a hand. When the lower elastic ring 402*b* is inserted into the body cavity 92 from the incision 91 formed in the body wall 90, and then the hand releases the elastic ring, the lower elastic ring 402*b* is restored to the original shape within the body cavity 92. As a result, as shown in FIG. 7, the lower elastic ring 402*b* is disposed around the incision 91 inside the body wall 90, while the upper elastic ring 402*a* is disposed around the incision 91 outside the body wall 90. The incision 91 is pressed and expanded into the circle shape by the silicon rubber sheet 401 located between the upper elastic ring 402*a* and the lower elastic ring 402*b*. Note that the annular member 40 for use is preferably selected depending on the size of the incision 91, the thickness of the body wall 90, and the like.

<2. Insertion of Framed Structure 20 and Sheet Member 30>

As shown in FIG. 8, the framed structure 20 in the contracted state is inserted into the body cavity 92 through the opening 43 of the annular member 40. When using the cylindrical member 70, one end 71 of the cylindrical member 70 is pushed into the body cavity 92 through the opening 43 of the annular member 40 as indicated by the arrow while holding the side of the other end 72 of the cylindrical member 70, so that the framed structure 20 can be inserted into the body cavity 92. As to the framed structure 20, the elongated parts 201 can be made extremely close to each other by significantly bending the curved parts 202. Thus, the framed structure 20 can be inserted into the body cavity 92 even through the small incision 91.

Further, as can be seen from FIG. 8, the framed structure 20 in the contracted state has the lower ends 201*b* of the elongated parts 201 gathered together, whereby the framed structure 20 can be easily inserted into a space between or among a plurality of surgical obstructions 95 within the body cavity 92. The lower edge part 32 of the sheet member 30 is attached to the lower ends 201*b* of the elongated parts 201 in the framed structure 20. Thus, when inserting the framed structure 20 into the body cavity 92, the sheet member 30 is drawn with the framed structure 20 and inserted into the body cavity 92.

<3. Deployment of Framed Structure 20>

After completely inserting the framed structure 20 and the sheet member 30 into the body cavity 92, the cylindrical member 70 is removed from the framed structure 20 as indicated by the arrow in FIG. 9. In this embodiment, since the curved parts 202 are formed of elastic tubes or the like, the curved parts 202 are elastically restored when removing the cylindrical member 70 from the framed structure 20, so that the framed structure 20 can be automatically deployed.

When the framed structure 20 cannot be deployed sufficiently only by the elasticity of the curved parts 202, an organ retraction balloon or the like, which is used in an endoscopic operation, can be utilized to assist in the deployment of the framed structure 20.

When the curved parts 202 are formed of plastically deformable elongated material, the framed structure 20 is not automatically deployed. In this case, the organ retraction balloon can be used to deploy the framed structure 20.

When using a balloon 81, as shown in FIG. 10, the balloon 81 in the contracted state is inserted into the body cavity via an insertion port 25 of the framed structure 20. The term "insertion port 25" as used herein means a region (hatched part) enclosed by the curved parts 202 as shown in FIG. 3. When the balloon 81 is inflated, the framed structure 20 is expanded, whereby the surgical obstructions 95 located around the framed structure 20 are displaced (see FIG. 11).

After completion of the deployment of the framed structure 20, the balloon 81 is returned to the contracted state and taken out of the body through the insertion port 25 of the framed structure 20 and the opening 43 of the annular member 40 (see FIG. 12). Material for the curved part 202 is preferably selected so that even after removing the balloon, the framed structure 20 can maintain its expanded state by the curved parts 202 of the framed structure 20. Thus, the surgical obstructions 95 can be maintained in the displaced state by the framed structure 20 even after taking out the balloon 81. The inside and lower side of the framed structure 20 in the deployed state become the operation field 12.

Even only the framed structure 20 can displace the surgical obstructions 95, but covering the framed structure 20 with the sheet member 30 can effectively prevent the surgical obstructions 95 from invading the operation field 12 through the space between the adjacent elongated parts 201.

<4. Supply of Perfusate L and Underwater Operation>

As shown in FIG. 13, the upper edge part of the water storage member 50 is fixed to a support member 75 with clips 76 or the like. Then, a perfusate L (e.g., normal saline solution) is charged into the water storage member 50 through an injection pipe 61. The perfusate L is stored in the main body 51 of the water storage member 50 and then flows into the body cavity 92 through the communication port 53. The perfusate L flowing into the body cavity 92 is drawn to the outside through a suction pipe 62, which is inserted into the body cavity 92.

Note that in the framed structure 20 including the elastic tubes 21 to 24, a part or all of the elastic tubes 21 to 24 may be provided with a connection point, to which the suction pipe 62 is connected, whereby the framed structure 20 can also be utilized as a part of the suction pipe 62 for the perfusate L.

When the water storage member 50 is formed of a soft sheet, the water storage member 50 is deformed by the weight of the perfusate L. The deformed water storage member 50 is brought into intimate contact with the body surface around the annular member 40. Thus, the effect of preventing the leakage of the liquid from the interface between the annular member 40 and the incision 91 can be expected.

In the endoscopic operation, the observation with ultrasound imaging (echo) is sometimes performed, too, together with the observation with an endoscope 82. To use the echo, an air layer must not be present between a probe and a subject to be observed. Here, the water storage member 50 filled with the perfusate L is in intimate contact with the body surface, and the body cavity 92 is filled with the perfusate L. Thus, a probe 84 is immersed into the perfusate L stored in the water storage member 50, and the tip end of the probe 84 is brought into contact with a contact surface between the water storage member 50 and the body surface, whereby the organ in the body cavity 92 can be observed with the echo.

The operation target part 94 undergoes the operation (for example, enucleation of the operation target part 94 and the like) while the perfusate L is being perfused sufficiently.

Surgical instruments, such as the endoscope 82 and the electric scalpel 83, are inserted into the body cavity 92 through the opening 43 of the annular member 40, and are further caused to approach operation target part 94 through the insertion port 25 of the framed structure 20. The operation target part 94 is observed with the endoscope 82. The electric scalpel 83 performs the operation (e.g., enucleation of the operation target part 94 and the like) on the operation target part 94.

In the underwater operation, there occurs a phenomenon in which the organ floats and is suspended in the perfusate L. Thus, in this kind of operation, organs (surgical obstructions 95) other than the operation target part 94 are more likely to invade the operation field 12, compared to the general operation. The presence of the surgical obstructions 95 can make it difficult to identify the operation field 12 or interrupt the operation of the surgical tools 82 and 83. In such a case, it is necessary to move the surgical obstructions 95 away from the operation field 12. However, in the endoscopic operation, the surgical obstructions 95 cannot be removed with a hand, and it takes a long time to move the surgical obstructions 95, which can lead to an increase in the operation time period. Thus, it is important to maintain the prevention of invasion of the surgical obstructions 95 into the operation field 12.

Here, by using the operation field-securing device 10, the framed structure 20 and the sheet member 30 hold the surgical obstructions 95 outside the framed structure 20, so that the surgical obstructions 95 are less likely to invade the operation field 12. Consequently, the operation can be completed in an appropriate operation time period.

The continuous perfusion of the perfusate L during the operation has some advantages.

When bleeding occurs in the body cavity, the perfusate L supplied into the body cavity 92 becomes turbid due to the blood, which can temporarily degrade the visibility of the operation field 12. By continuously perfusing the perfusate L, the perfusate L with the blood mixed therein is discharged from the suction pipe 62, thereby immediately achieving good visibility. In particular, the tip end of the suction pipe 62 is preferably disposed under the operation target part 94. Because of this, the blood or the like originated from the surroundings of the operation target part 94 is more likely to be discharged from between the endoscope 82 and the operation target part 94, thus making it possible to maintain the good visibility.

Furthermore, by continuously perfusing the perfusate L, the state where the blood flows from a bleeding point can be easily recognized visually, thereby making it possible to easily specify the bleeding point. The underwater operation can restrain the amount of bleeding from the bleeding point by water pressure of the perfusate L.

After the end of the underwater operation, the supply of the perfusate L from the injection pipe 61 is terminated, and then the perfusate L within the body cavity 92 and the water storage member 50 is discharged through the suction pipe 62.

<5. Removal of Framed Structure 20>

As shown in FIG. 14, the framed structure 20 is brought into the contracted state and then pulled out of the body through the opening 43 of the annular member 40.

The framed structure 20 can be easily transformed from the deployed state as shown in FIG. 13 into the contracted state as shown in FIG. 14. When observing the framed structure 20 in the deployed state shown in FIG. 13 through the opening 43 of the annular member 40, the curved parts 202 of the framed structure 20 can be visually recognized through the opening 43 as shown in FIG. 15. As can be seen from FIG. 13, the curved parts 202 are positioned immediately under the opening 43. This is because the curved parts 202 are convex toward the side opposite to the elongated parts 201 (that is, convex upward). When the elongated parts 201 are inserted toward the deep part of the body cavity 92, the curved parts 202 are positioned closer to the body surface. Thus, it is relatively easy to compress and deform the curved parts 202 with a hand or an instrument, thereby bringing the framed structure 20 into the contracted state. When the strength of the body wall 90 around the incision 91 is sufficiently high, the curved parts 202 only need to be pulled out of the opening 43. Consequently, the framed structure 20 is compressed inward by the opening 43, so that the framed structure 20 is brought into the contracted state.

The lower edge part 32 of the sheet member 30 is attached to the lower ends 201*b* of the elongated parts of the framed structure 20. Thus, when removing the framed structure 20 out of the body, the sheet member 30 can be also drawn out of the body by being pulled with the framed structure 20.

First Modified Embodiment

FIG. 16 shows a first modified embodiment of the operation field-securing device 10. An operation field-securing device 101 according to this modified embodiment differs from the embodiment mentioned above in that the sheet member 30 is provided with a cut away part 36, which is disposed between the adjacent elongated parts 201 of the framed structure 20. The structures of the other components in this modified embodiment are the same as those in the operation field-securing device 10 according to the first embodiment.

In some cases, the operation is required to be performed not only on the organ positioned in the operation field 12 (see FIG. 12) secured by the operation field-securing device 101, but also on the other organ (s) positioned beside the operation field 12. In the operation field-securing device 101 according to this modified embodiment, the cut away part 36 provided in the sheet member 30 is positioned between the elongated parts 201 of the framed structure 20, thereby enabling the access to the organ(s) outside the operation field 12 via the cut away part 36.

The organ as the operation target part 94 is coupled with another organ as the surgical obstruction 95 by a tract in some cases. In the operation field-securing device 101 according to this modified embodiment, the cut away part 36 of the sheet member 30 is disposed between the operation target part 94 and the surgical obstruction 95, so that the operation target part 94 can be disposed inside the operation field 12, while the surgical obstruction 95 can be disposed outside the operation field 12.

Second Modified Embodiment

FIG. 17 shows a second modified embodiment of the operation field-securing device. An operation field-securing device 102 according to this modified embodiment differs from the embodiment mentioned above in that the sheet member 30 includes two sheet members. The structures of the other components in this modified embodiment are the same as those in the operation field-securing device 10.

As shown in FIG. 17, the sheet member 30 in the operation field-securing device 102 includes a first sheet member (outer sheet member) 301 disposed on the outer side of the elongated parts 201 and a second sheet member (inner sheet member) 302 disposed on the inner side of the elongated parts 201 in the deployed state. In the first sheet member 301, an upper edge part thereof is attached to the annular member 40, and a lower edge part 3012 thereof is attached to the lower ends 201*b* of the elongated parts of the framed structure 20. Meanwhile, in the second sheet member 302, an upper edge part thereof is attached to the annular member 40, but a lower edge part 3022 thereof is not fixed to the framed structure 20. Because of this, the framed structure 20 can be accommodated in the water storage member 50 through the opening 43 of the annular member 40.

In the use of the operation field-securing device 102, a suction port 621 of the suction pipe 62 is disposed in a space 303 between the outer sheet member 301 and the inner sheet member 302. The rectifying effect of the perfusate L can be enhanced in the operation field 12 (mainly, inside the framed structure 20). Thus, the turbidity of the perfusate L can be expected to be suppressed during the operation. The rectifying effect will be described in detail below with reference to FIG. 18.

As shown in FIGS. 18(*a*) and 18(*b*), the perfusate L stored in the water storage member 50 flows into the body cavity 92 through the opening 43 of the annular member 40.

With the operation field-securing device 10, as shown in FIG. 18(*b*), the suction pipe 62 is disposed in the sheet member 30 to create a perfusion route FL1 toward one point of the suction port 621. Consequently, in the vicinity of the suction port 621, turbulent flow is likely to occur.

Meanwhile, in the operation field-securing device 102 of this modified embodiment, as shown in FIG. 18(*a*), the suction port 621 of the suction pipe 62 is disposed in the space 303 between the outer sheet member 301 and the inner sheet member 302. In a perfusion route FL2, the perfusate L is drawn over a wide range toward an elongated region located between the lower edge part 3012 of the outer sheet member 301 and the lower edge part 3022 of the inner sheet member 302 and then drawn through the suction port 621. That is, in the operation field 12, turbulent flow is less likely to occur.

Thus, in this modified embodiment, the rectifying effect of the perfusate L can be expected within the framed structure 20, thereby making it possible to reduce the turbidity of the perfusate L caused by bleeding during the operation.

Materials suitable for use in the respective components in the first embodiment and the first and second modified embodiments will be described below. Note that these materials for use in the respective components are inserted into the body and thus need to be those that can be subjected to sterilization and have high biological safety.

(Elongated Part 201, Curved Part 202) Each of the elongated part 201 and the curved part 202 in use can be a hollow elongated member (tube) or solid elongated member.

Examples of the tube suitable for use include an elastic tube made of resins such as polyvinyl chloride, polyethylene, fluororesin, silicone rubbers, synthetic rubbers, natural rubbers and polyurethane, and a plastically deformable tube made of metals such as stainless steel and shape-memory alloys.

The solid elongated member in use can be, for example, a wire made of resins, such as polyvinyl chloride, polyethylene, fluororesin, silicone rubbers, synthetic rubbers, natural rubbers and polyurethane, and a wire made of metals, such as stainless steel.

In particular, the tube made of silicone rubbers, polyethylene, or polyurethane, is preferable because of its high stability and biological compatibility.

All of three or more elongated parts 201 may be formed of the same material, or parts or all of them may be formed of different materials.

Parts or all of three or more curved parts 202 may be formed of different materials. However, all these curved parts are preferably formed of the same material because the framed structure 20 is isotropically deployed and contracted with ease.

The elongated part 201 and the curved part 202 can be formed of different materials, but are preferably formed of the same material.

(Sheet Member 30, First Sheet Member 301, Second Sheet Member 302)

Each of the sheet member 30, the first sheet member 301 and the second sheet member 302 can be formed of a soft sheet material. Suitable sheet materials can include sheet materials made of, for example, resins, such as polyvinyl chloride, silicone rubbers, synthetic rubbers, natural rubbers, polyethylene and polyurethane. In particular, the sheet member is preferably formed of a transparent sheet material. The first sheet member 301 and the second sheet member 302 may be formed of the same sheet material or otherwise different sheet materials.

(Fixing Member 26)

The fixing member 26 may be any member that can be subjected to sterilization and can fix two tubes. The fixing member 26 suitable for use is, for example, a resin binding band, a surgical suture thread, a metal wire, a metal connector, a medical adhesive, or the like.

(Annular Member 40)

The annular member 40 in use can be, for example, a metal retractor, a retractor made of a synthetic resin (e.g., a silicone rubber retractor), or the like. In particular, the silicone rubber retractor can be in intimate contact with the incision, thereby making it possible to prevent the leakage of liquid when using the operation field-securing device for the underwater operation.

(Water Storage Member 50)

The water storage member 50 can be formed of a sheet material. Suitable sheet materials can include sheet materials made of, for example, resins, such as polyvinyl chloride, silicone rubbers, synthetic rubbers, natural rubbers, polyethylene and polyurethane. To make the water storage member 50 standby itself, the water storage member may be provided with a frame body.

Although some embodiments according to the present invention have been exemplified above, it is apparent that the present invention is not limited to the above-mentioned embodiments and can have any form without departing from the scope of the present invention.

DESCRIPTION OF REFERENCE NUMERALS

10 Operation field-securing device
12 Operation field
20 Framed structure
21, 22, 23, 24 Tube
201 Elongated part
202 Curved part
26 Fixing member
30 Sheet member
40 Annular member
50 Water storage member
70 Cylindrical member
90 Body wall
91 Incision
92 Body cavity

The invention claimed is:

1. An operation field-securing device for securing an operation field by being deployed in a body cavity, the operation field-securing device comprising:

at least three elongated parts extending radially in a deployed state;
curved parts, the number of which is the same as that of the elongated parts;
a sheet member configured to cover a space between the elongated parts when being deployed; and
an annular member to which a first edge part of the sheet member is attached, wherein
each pair of the two adjacent elongated parts is connected at one ends thereof by the curved part,
a second edge part of the sheet member is attached to the other ends of the elongated parts,
each of the curved parts is convex toward a side opposite to the elongated part,
in the deployed state, the curved parts are arranged circumferentially,
by deforming the curved parts, the operation field-securing device is capable of being brought into either one of a contracted state where a distance between the adjacent elongated parts is shortened and the deployed state where the distance between the adjacent elongated parts is expanded,
the elongated parts and the curved parts are not directly fixed to the annular member, but are indirectly fixed to the annular member via the sheet member, whereby, in the contracted state, the elongated parts and the curved parts are allowed to pass from one side to another side of the annular member through an inside of the annular member,
the annular member includes a first annular member and a second annular member to be fitted into an inside of the first annular member, and
the first edge part of the sheet member is sandwiched between the first annular member and the second annular member.

2. The operation field-securing device according to claim 1, wherein each of the elongated parts includes two elongated elements arranged in parallel and fixed to each other,
one end of one of the two elongated elements is connected to one end of the curved part, while one end of the other of the two elongated elements is connected to another end of another curved part, and
the curved part and two of the elongated elements connected to both ends of the curved part are configured from one tube.

3. The operation field-securing device according to claim 2, wherein the tube is provided with a connection point for connecting a suction pipe.

4. The operation field-securing device according to claim 1, wherein each of the curved parts is made of an elastically deformable member, and
the curved parts are configured to be elastically deformed in the contracted state and to be elastically restored from the contracted state to the deployed state.

5. The operation field-securing device according to claim 1, wherein the sheet member includes a first sheet member disposed on an outer side of the elongated parts and a second sheet member disposed on an inner side of the elongated parts when being deployed.

6. The operation field-securing device according to claim 5, further comprising a suction pipe, wherein a suction port of the suction pipe is disposed in a space between the first sheet member and the second sheet member.

7. The operation field-securing device according to claim 1, wherein the annular member is an annular retractor.

8. The operation field-securing device according to claim 7, further comprising a water storage member with a communication port, wherein the communication port is water-tightly connected to the retractor.

9. The operation field-securing device according to claim 8, wherein the water storage member is formed of a soft sheet.

10. The operation field-securing device according to claim 1, wherein the other ends of the elongated parts are terminated without connecting with the curved parts.

11. An operation field-securing device for securing an operation field by being deployed in a body cavity, the operation field-securing device comprising:
   at least three elongated parts extending radially in a deployed state;
   curved parts, the number of which is the same as that of the elongated parts;
   a sheet member configured to cover a space between the elongated parts when being deployed; and
   an annular member to which a first edge part of the sheet member is attached, wherein
   each pair of the two adjacent elongated parts is connected at one ends thereof by the curved part,
   a second edge part of the sheet member is attached to the other ends of the elongated parts,
   each of the curved parts is convex toward a side opposite to the elongated part,
   in the deployed state, the curved parts are arranged circumferentially,
   by deforming the curved parts, the operation field-securing device is capable of being brought into either one of a contracted state where a distance between the adjacent elongated parts is shortened and the deployed state where the distance between the adjacent elongated parts is expanded, and
   the elongated parts and the curved parts are not directly fixed to the annular member, but are indirectly fixed to the annular member via the sheet member, whereby, in the contracted state, the elongated parts and the curved parts are allowed to pass from one side to another side of the annular member through an inside of the annular member, and
   the other ends of the elongated parts are terminated without connecting with the curved parts.

12. The operation field-securing device according to claim 11, wherein each of the elongated parts includes two elongated elements arranged in parallel and fixed to each other,
   one end of one of the two elongated elements is connected to one end of the curved part, while one end of the other of the two elongated elements is connected to another end of another curved part, and
   the curved part and two of the elongated elements connected to both ends of the curved part are configured from one tube.

13. The operation field-securing device according to claim 11, wherein each of the curved parts is made of an elastically deformable member, and
   the curved parts are configured to be elastically deformed in the contracted state and to be elastically restored from the contracted state to the deployed state.

14. The operation field-securing device according to claim 11, wherein the sheet member includes a first sheet member disposed on an outer side of the elongated parts and a second sheet member disposed on an inner side of the elongated parts when being deployed.

15. The operation field-securing device according to claim 14, further comprising a suction pipe, wherein a suction port of the suction pipe is disposed in a space between the first sheet member and the second sheet member.

16. The operation field-securing device according to claim 11, wherein the annular member is an annular retractor.

17. The operation field-securing device according to claim 16, further comprising a water storage member with a communication port, wherein the communication port is water-tightly connected to the retractor.

18. The operation field-securing device according to claim 17, wherein the water storage member is formed of a soft sheet.

* * * * *